United States Patent
Van Antwerp et al.

(10) Patent No.: US 6,319,540 B1
(45) Date of Patent: Nov. 20, 2001

(54) DETECTION OF BIOLOGICAL MOLECULES USING CHEMICAL AMPLIFICATION AND OPTICAL SENSORS

(75) Inventors: William Peter Van Antwerp, Valencia; John Joseph Mastrototaro, Los Angeles, both of CA (US)

(73) Assignee: MiniMed Inc., Northridge, CA (US)

( * ) Notice: Subject to any disclaimer, the term of this patent is extended or adjusted under 35 U.S.C. 154(b) by 0 days.

(21) Appl. No.: 09/401,147

(22) Filed: Sep. 22, 1999

Related U.S. Application Data

(63) Continuation of application No. 08/752,945, filed on Nov. 21, 1996, now Pat. No. 6,011,984.
(60) Provisional application No. 60/007,515, filed on Nov. 22, 1995.

(51) Int. Cl.[7] .................................................. A61L 5/103
(52) U.S. Cl. ....................... 427/2.13; 427/2.11; 427/2.12; 428/704
(58) Field of Search ................................ 427/2.11, 2.12, 427/2.13, 384; 428/704

(56) References Cited

U.S. PATENT DOCUMENTS

| | | | |
|---|---|---|---|
| 3,912,595 | * 10/1975 | Philipp et al. | 195/66 R |
| 4,401,122 | 8/1983 | Clark, Jr. | 128/635 |
| 4,428,366 | 1/1984 | Findl et al. | 128/15 |
| 4,496,722 | 1/1985 | Gallop et al. | 544/69 |
| 4,655,225 | 4/1987 | Daehn et al. | 128/633 |
| 4,680,268 | 7/1987 | Clark, Jr. | 435/291 |
| 4,805,623 | 2/1989 | Jobsis | 128/633 |
| 4,875,486 | 10/1989 | Rapoport et al. | 128/653 |
| 4,882,492 | 11/1989 | Schlager | 250/346 |
| 4,974,929 | 12/1990 | Curry | 350/96.29 |
| 5,028,787 | 7/1991 | Rosenthal et al. | 250/341 |
| 5,054,487 | 10/1991 | Clarke | 128/633 |
| 5,070,874 | 12/1991 | Barnes et al. | 128/633 |
| 5,077,476 | 12/1991 | Rosenthal | 250/341 |
| 5,086,229 | 2/1992 | Rosenthal et al. | 250/341 |
| 5,101,814 | 4/1992 | Palti | 128/634 |
| 5,108,502 | * 4/1992 | Pawlowski et al. | 106/22 |
| 5,112,124 | 5/1992 | Harjunmaa et al. | 356/39 |
| 5,137,833 | 8/1992 | Russell | 436/94 |
| 5,196,709 | 3/1993 | Berndt et al. | 250/458.1 |
| 5,203,328 | 4/1993 | Samuels et al. | 128/633 |
| 5,209,838 | * 5/1993 | Sleppy et al. | 208/179 |
| 5,240,602 | * 8/1993 | Hammen | 210/198.2 |
| 5,246,867 | 9/1993 | Lakowicz et al. | 436/95 |
| 5,279,543 | 1/1994 | Glikfeld et al. | 604/20 |
| 5,281,825 | 1/1994 | Berndt et al. | 250/458.1 |
| 5,342,789 | 8/1994 | Chick et al. | 436/501 |
| 5,353,790 | 10/1994 | Jacques et al. | 128/633 |
| 5,362,307 | 11/1994 | Guy et al. | 604/20 |
| 5,409,835 | 4/1995 | Lakowicz et al. | 436/79 |
| 5,445,611 | 8/1995 | Eppstein et al. | 604/49 |
| 5,458,140 | 10/1995 | Eppstein et al. | 128/632 |
| 5,476,094 | 12/1995 | Allen et al. | 128/634 |
| 5,495,850 | 3/1996 | Zuckerman | 128/634 |
| 5,503,770 | * 4/1996 | James et al. | 252/301.16 |
| 5,512,246 | 4/1996 | Russell et al. | 422/57 |
| 5,628,310 | 5/1997 | Rao | 600/317 |
| 6,040,194 | 3/2000 | Chick et al. | 436/501 |
| 6,254,829 | 7/2001 | Hartmann et al. | 422/82.06 |
| 6,254,831 | 7/2001 | Barnard et al. | 422/82.08 |
| 6,256,522 | 7/2001 | Schultz | 600/317 |

FOREIGN PATENT DOCUMENTS

| | | |
|---|---|---|
| 0 673 622 | 1/1989 | (EP) . |
| 0 693 271 | 1/1996 | (EP) . |
| 0729 962 | 9/1996 | (EP) . |
| 2 284 809 | 6/1995 | (GB) . |
| WO 82/01804 | 5/1982 | (WO) . |
| WO 96/03074 | 2/1996 | (WO) . |
| WO 97/19188 | 5/1997 | (WO) . |

OTHER PUBLICATIONS

Burnett, et al. "Synthesis of a Fluroescent Boronic Acid which Reversibly Binds to Cell Walls and a Diboronic Acid which Agglutinates Erythrocytes." Biochemical and Biophysical Research Communications, vol. 96, No. 1, Sep. 1980.*
Arnold et al. *Anal. Chem.*, 62:1457–64 (1990).
Bostick et al. *Analytical Chemistry*, 47:447–52 (1975).
DCCT Research Group. *New England Journal of Medicine*, 329:977–86 (1993).
Falasca et al. *Biochemica et Biophysica Acta*, 577:71–81 (1979).
Gough et al. *Diabetes*, 44:1005–9 (1995).
Guilbault et al. *Anal. Chem.*, 40:190 (1968).
Hawkins et al. *J Am. Chem. Soc.*, 82:386–366 (1960).
James et al. *J. Chem. Soc., Chem. Commun.*, pp. 477–478 (1994).
James et al. *J. Am. Chem. Soc.*, 117:8982–87 (1995).
James et al. *Nature*, 374:345–47 (1995).
Lakowicz et al. Sensors and Actuators B., 11:133–143 (1993).
Lakowicz et al. J. Fluorescence, 4 (1):117–36 (1994).
Lin et al. *J. Org. Chem.*, 44 (25):4701–03 (1979).
Marquardt et al. *Anal. Chem.* 65:3271–78 (1993).
Monroe. Am. Clin. Lab., 8 (12):8–16 (1989).
Nakashima et al. *Chemistry Letters*, pp. 1267–1270 (1994).

(List continued on next page.)

Primary Examiner—Margaret G. Moore
(74) Attorney, Agent, or Firm—Gates & Cooper LLP

(57) ABSTRACT

Methods are provided for the determination of the concentration of biological levels of polyhydroxylated compounds, particularly glucose. The methods utilize an amplification system that is an analyte transducer immobilized in a polymeric matrix, where the system is implantable and biocompatible. Upon interrogation by an optical system, the amplification system produces a signal capable of detection external to the skin of the patient. Quantitation of the analyte of interest is achieved by measurement of the emitted signal. Specifically, the analyte transducer immobilized in a polymeric matrix can be a boronic acid moiety.

13 Claims, 14 Drawing Sheets

OTHER PUBLICATIONS

Pilsof et al. *Anal. Chem.*, 54:1698–1701 (1982).
Reach et al. *Anal. Chem.*, 64 (6):381–86 (1992).
Sandanayake et al. Chemistry Letters, pp. 139–140 (1995).
Uziel et al. *Biochem. and Biophys. Res. Commun.*, 180 (3):1233–49 (1991).
Yoon et al. *J. Am. Chem. Soc.*, 114:5874–75 (1992).

* cited by examiner

DETECTION OF BIOLOGICAL MOLECULES USING CHEMICAL AMPLIFICATION AND OPTICAL SENSORS This application is a Continuation Application of and claims the benefit of U.S. patent application Ser. No. 08/752,945, filed Nov. 21, 1996, now U.S. Pat. No. 6,011,984, which is a Continuation-In-Part of U.S. Provisional Application Ser. No. 60/007,515, filed Nov. 22, 1995, and is related to U.S. patent application Ser. No. 08/721,262, filed Sep. 26, 1996, now U.S. Pat. No. 5,777,060 which is a Continuation-In-Part of U.S. patent application Ser. No. 08/410,775, filed Mar. 27, 1995, now abandoned the disclosures of which are incorporated by reference.

The United States Government may have rights in inventions disclosed in this application pursuant to Contract No. W-7405-ENG-48 between the United States Department of Energy and the University of California for the operation of Lawrence Livermore National Laboratory.

FIELD OF THE INVENTION

This invention relates generally to biological sensors. More specifically, this invention relates to minimally invasive amplification systems and optical sensors capable of detecting polyhydroxylated compounds such as glucose.

BACKGROUND OF THE INVENTION

An essential tool for the care of the diabetic patient is the measurement of blood glucose. Recently, the NIDDK (National Institutes of Diabetes and Digestion and Kidney Diseases) has released the results of a large clinical trial, the DCCT (Diabetes Control and Complications Trial) that shows conclusively that improved blood glucose control reduces the risk of long term complications of diabetes. See, DCCT Research Group, *N. Engl. J. Med.* 329:977–986 (1993).

Current technology requires that a blood sample be obtained for measurement of blood glucose levels. Samples of venous blood can be obtained from the patient for this measurement, but this method is limited to only a few samples per day, and is not practical for the care of outpatients.

Self monitoring of capillary blood glucose is practical, but still requires multiple and frequent skin punctures. Consequently, most patients perform 2–6 tests per day depending on their personal circumstances and medical condition. Self monitoring results are influenced by technique errors, variability of sample volume and impaired motor skills (important with hypoglycemic episodes). The patient must interrupt other activities to perform the task of blood glucose measurement.

The concept of an implantable sensor to continuously measure the glucose levels in holter monitor type applications and in ambulatory diabetic individuals has existed for several decades. For a recent discussion, see Reach, et al., *Anal. Chem.* 64:381–386 (1992). The primary focus has been to overcome the disadvantages of capillary blood glucose self monitoring by developing a glucose sensor, which at the very least, would provide more frequent and easily acquired glucose information. In addition, the sensor could function as a hypoglycemic and hyperglycemic alarm, and ultimately serve as the controller for an artificial endocrine pancreas. The potential limitations of this approach include the limited life of the enzyme, glucose oxidase, the limited lifetime of the sensor (2–3 days), and the need to wear the device.

The concept of a non-invasive glucose sensor has received significant media and technical attention over the past several years. The basic scientific goal has been to utilize near infrared (NIR) spectrophotometry to detect the absorbance properties of the glucose molecule. The inherent problem with this approach is that the glucose signal is weak and is masked by other body constituents. Moreover, if it is possible to detect glucose, the system will most likely rely upon expensive optics and significant computing power, resulting in a large, expensive device which requires frequent recalibration to the patient and provides intermittent data.

Some of the approaches to non-invasive blood glucose measurement are described in U.S. Pat. Nos. 4,428,366, 4,655,225, 4,805,623, 4,875,486, 4,882,492, 5,028,787, 5,054,487, 5,070,874, 5,077,476, 5,086,229, and 5,112,124, the disclosures of each being incorporated herein by reference.

Most of these approaches involve the use of transdermal infrared or near infrared radiation in either a transmission or reflectant mode. In spite of the large number of patents and intense efforts by at least thirty major companies, no devices have been successfully implemented in the field.

The problems with these approaches are well known and described in detail by Marquardt, et al., *Anal. Chem.*, 65:3271 (1993) and Arnold, et al., *Anal. Chem.*, 62:1457 (1990). Marquardt, et al. have shown that in a simple aqueous solution, the absorbance of a 13 mM glucose solution (234 mg/dl) gave a signal with a S/N ratio of about 2. In a protein containing matrix, the actual signal from glucose cannot be detected without considerable manipulation of the data using a partial least squares approach. Such small signal to noise ratios are not practical for developing robust simple instrumentation. Furthermore, the device used in this research is a large spectrophotometer that must be able to scan over reasonably broad wavelength ranges.

In contrast to these purely non-invasive optical approaches, an implant containing a transducer chemical whose optical properties are strongly modulated by recognition of the target analyte will result in a large amplification of the optical signal. It is in this sense that the term "chemical amplification" is used throughout this application. For instance, U.S. Pat. No. 4,401,122 describes an implanted enzymatic sensor that measures the $H_2O_2$ produced when glucose and oxygen react in the presence of the enzyme glucose oxidase. This approach is limited by profound biocompatibility concerns, particularly changes in stability related to glucose diffusion to the sensor and the lifetime of an enzyme in an implanted environment. Further concerns using enzymes are created because the large differential between $O_2$ and glucose concentrations in the body requires a glucose limiting outer membrane. This membrane limits not only the glucose, but the analytical signal as well.

One approach to solving the problems is described in U.S. Pat. No. 5,342,789. In this approach, a fluorescent labeled glycoprotein competes with glucose for binding to a differently fluorescent labeled lectin. Because there is some resonance energy transfer from one label to the other, the presence of glucose reduces the fluorescence intensity of the system. There are two major drawbacks to the system as described in the '789 patent. The first problem is that both labels are photoexcited by the same source; the background signal is significant. The second problem is related to the ability of the system to be implanted into the body. The resonance energy transfer requires diffusion of glucose to the lectin and diffusion of the labeled glycoprotein away from the lectin. In order for the system to have a reasonable time constant for physiological applications, the reagents must be in solution and free to diffuse via a concentration gradient. This makes the device difficult to implement reliably since a reservoir must be designed which allows glucose to diffuse in but prevents the proteins and lectin from diffusing out.

Accordingly, there has been a need for a glucose sensor able to measure glucose over the entire physiological range of 30 to 500+ mg/dl (1.6 to 28+ mM). It should provide continuous glucose information and be easy to use. The sensor would not require a sample of blood and would be pain free. From an analytical chemistry standpoint, both the accuracy and the precision would be greater than 95% and the sensor should be non-invasive or minimally invasive. From an instrumental point of view, the device should have a linear dynamic range of at least 200 and a signal to noise ratio of at least 50. Attainment of these figures will ensure that analytical precision and accuracy can be achieved. However, less sensitive instruments could be useful providing measurement of the analyte signals is accurate. The present invention fulfills these needs and provides other related advantages.

SUMMARY OF THE INVENTION

The present invention provides methods for the determination of biological levels of polyhydroxylated compounds, particularly glucose. The methods utilize an amplification system which is implantable and which produces a signal capable of detection, typically external to the skin of a mammal, for example, a human. The amplification system is an analyte transducer which is immobilized in a polymeric matrix. Generation of a signal by the amplification system is typically the result of interrogation by an optical source. Importantly, the signal does not require resonance energy transfer, but instead relies on electron transfer (e.g., molecular electron transfer or photoelectron transfer). Detection of the signal produced then determines the quantity of polyhydroxylated compound or analyte of interest.

There are therefore two important aspects of the invention. The first is an implantable amplification system (IAS) which includes amplification components which are immobilized in a polymer matrix, typically a biocompatible matrix, either by entrapment or by covalent attachment. The second aspect of the invention is an optical system which interrogates the immobilized amplification components to produce a detectable signal. In some embodiments, the optical system is a transdermal optical system, while in other embodiments a fiber optic system is used.

DETAILED DESCRIPTION OF THE INVENTION

The following abbreviations are used herein: dl, deciliter; DEG, diethylene glycol; DMF, dimethylformamide; IAS, implantable amplification system; PBS, phosphate buffered saline; THF, tetrahydrofuran; DI, deionized; PEG, poly (ethylene)glycol; mv, millivolts; mg, milligrams.

General

Figure 1:
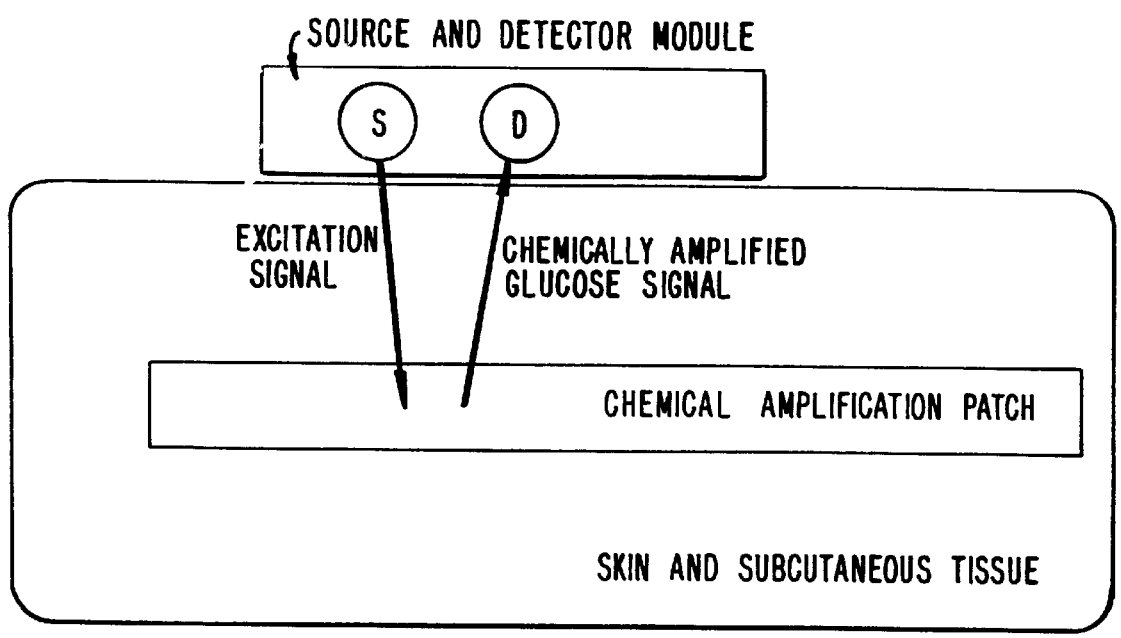
FIG. 1 shows a schematic of the optical glucose monitoring system.

The broad concept of the present invention is illustrated in FIG. 1. As can be seen, the basic scheme utilizes both a detector and source module which can be external to the skin. The source provides an excitation signal which interrogates a subcutaneous amplification system. The system then produces an amplified signal which is monitored by the external detector.

The amplification system can be implanted into a variety of tissues. Preferably, the system is implanted subcutaneously at a depth of from 1 to 2 mm below the surface of the skin. At this depth the system is most easily implanted between the dermis layer and the subcutaneous fat layer. These layers, in mammals are relatively easily separated and an amplification system (e.g., chemical amplification components in a biocompatible polymer) can be inserted into a small pocket created in a minor surgical procedure. The implanted system can be profused by capillary blood and made of a material through which glucose can easily diffuse. Alternatively, the amplification system can be placed in contact with other fluids containing the analyte of interest.

In one group of embodiments (illustrated in FIG. 1), the amplification system contains an immobilized chemical amplification component which may contain a fluorescent moiety providing a signal which is modulated by the local analyte concentration. A filter can also be incorporated into the system for the fluorescent photons (for those embodiments in which a fluorescent dye is used). The implanted amplification system is interrogated transdermally by a small instrument worn or placed over the implant. The small instrument contains a light source (e.g., a filtered LED) and a filtered detector (e.g., a photomultiplier tube, an unbiased silicon photodiode). The signal from the detector provides a continuous reading of the patient's analyte level which can also be used as input to, for example, an insulin pump or a visual reading for the patient. Alternative embodiments are described below (e.g., use of a fiber optic for interrogation of the amplification system).

Figure 2:
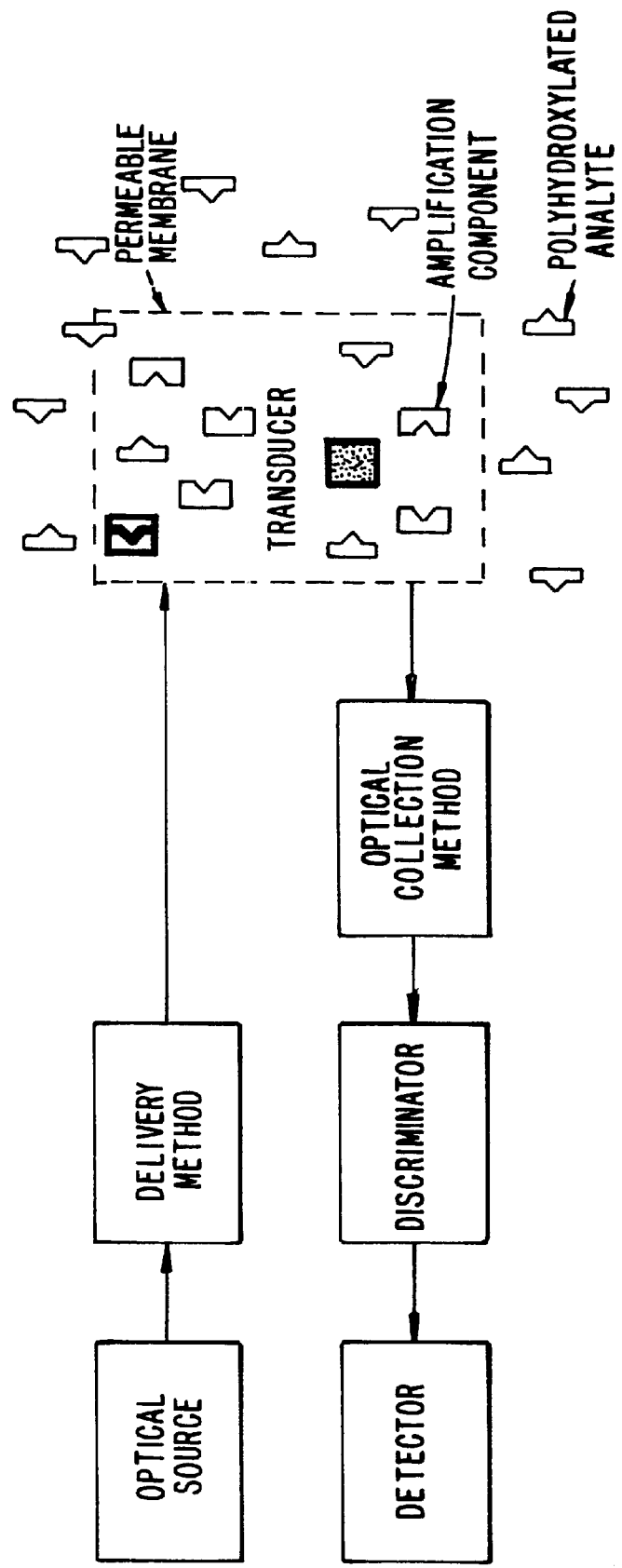
FIG. 2 illustrates a schematic of an optical analyte monitoring system which further illustrates the binding of a polyhydroxylated analyte to an amplification component following permeation into a biocompatible matrix.

FIG. 2 provides yet another schematic which illustrates the amplification system. According to this figure, the amplification system includes a permeable membrane, a matrix for immobilizing the amplification components, and the amplification components themselves. The polyhydroxylated analyte can then permeate the matrix, bind to the amplification components and produce a signal upon interrogation which is collected, filtered and detected. The optical sources can be a variety of light sources (e.g. laser diode, LED) and the light can be delivered to the amplification system via delivery methods which could include lenses and fiber optics. Alternatively, the optical interrogation can take place with transdermal illumination. The resultant signal can be collected, again via a fiber optic or lens, and sent to the detector, with the optional use of an intervening filter or discriminator.

In addition to the embodiments generally described in FIGS. 1–2, the present invention provides sensing systems and methods as generally illustrated in FIGS. 3–6.

Figure 3:
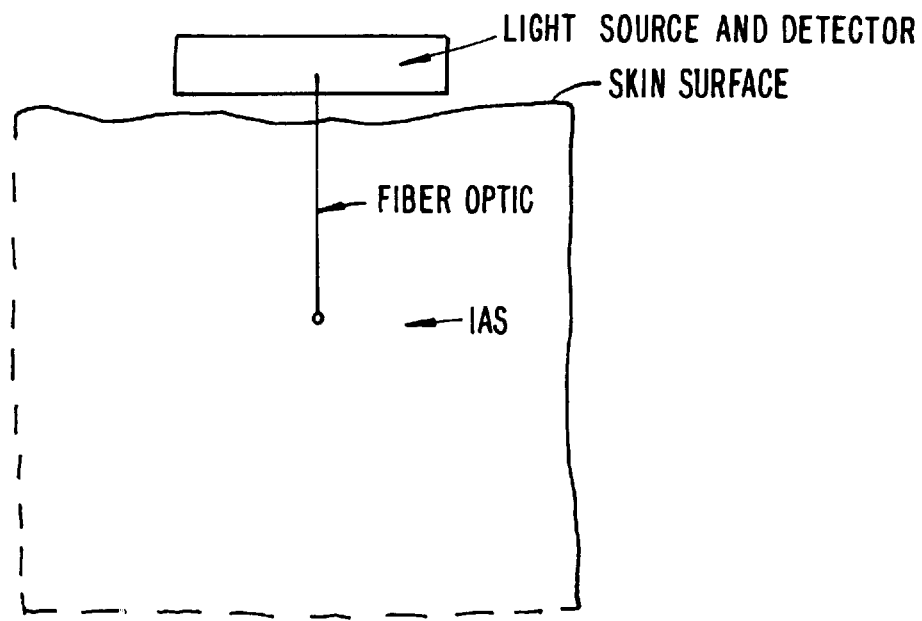
FIG. 3 illustrates one embodiment of the invention which uses a fiber optic bundle as a "light pipe" for interrogation of an implanted amplification system.

In FIG. 3, a light source is positioned external to the skin and the amplification system is placed at or coated on the distal end of a fiber optic, which is inserted through the skin into a subcutaneous layer. The fiber optic serves to conduct the light from the source to the amplification system, and then collects the light emitted from the amplification system and conducts it back to the detector.

Figure 4:
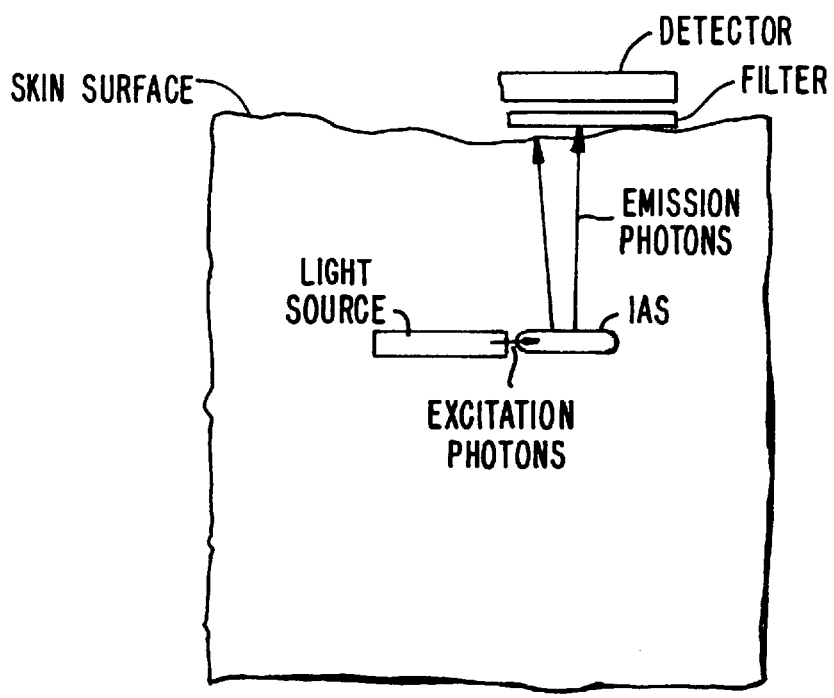
FIG. 4 illustrates another embodiment of the invention which uses a subcutaneous light source for interrogation of an implanted amplification system.
Figure 5:
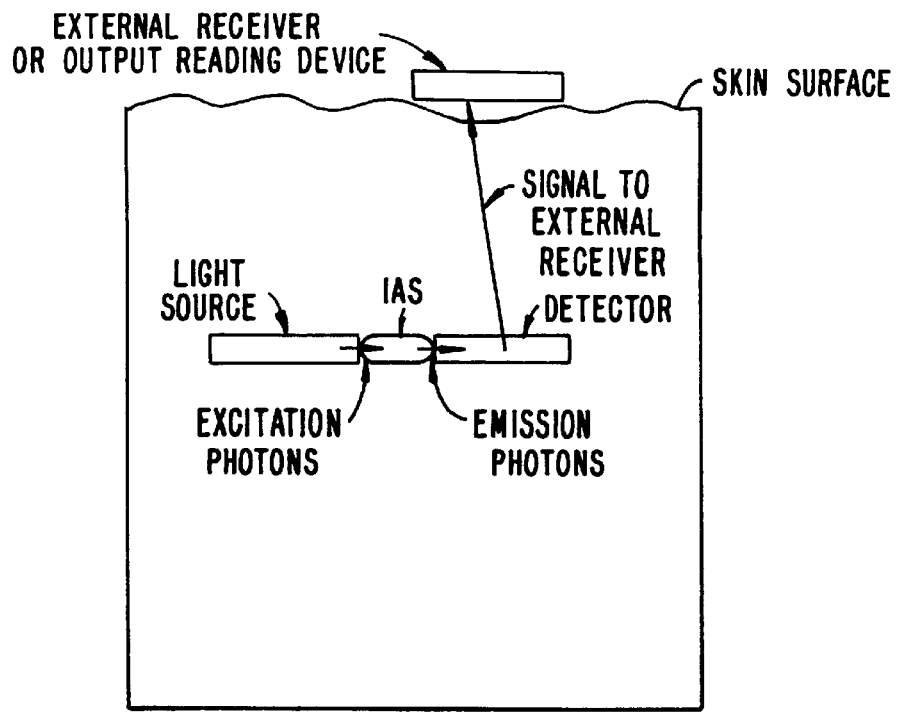
FIG. 5 illustrates another embodiment of the invention which uses a subcutaneous light source and detector to provide a completely subdermal analyte monitoring system.

Yet another embodiment is provided in FIG. 4. According to this figure, the light source is also implanted under the dermis. Upon interrogation of the IAS by the internal light source, the IAS provides a signal which is transdermally transmitted to an external detector.

In still another embodiment (FIG. 5), the light source and detector are both implanted under the dermis. The detector then provides transmission of the information to an output reading device which is external to the skin.

Figure 6:
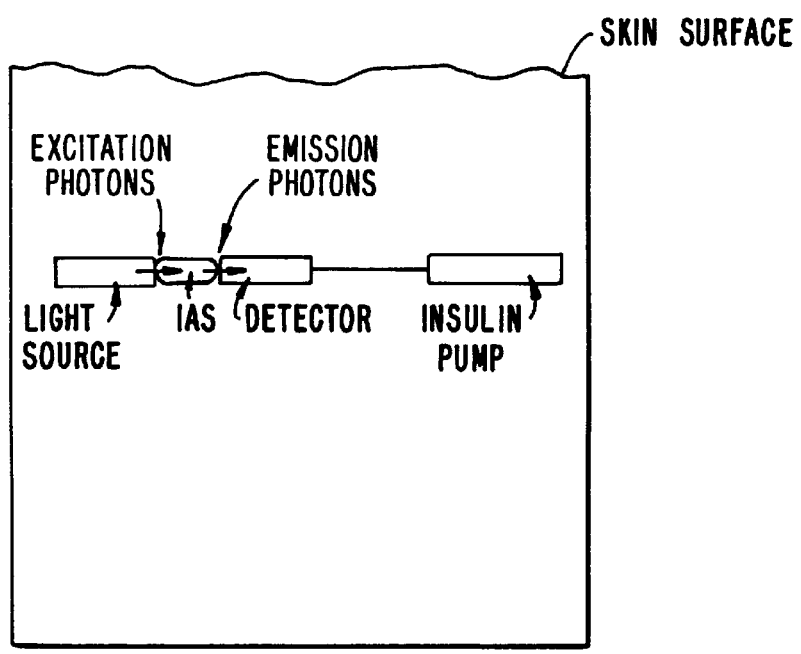
FIG. 6 illustrates another embodiment of the invention which uses a subcutaneous light source and detector to provide a completely subdermal analyte monitoring system which is coupled to an analyte source or medicament pump (e.g., an insulin pump) to provide a "closed loop" monitoring and supplementation system (e.g. an artificial pancreas).

Finally, for those embodiments in which glucose levels are determined, some aspects of the invention are directed to coupling of the detector signal to an insulin pump system in a "closed-loop" artificial pancreas (see FIG. 6).

As a result of the above descriptions, the biosensors of the present invention comprise two important components. The first component is an implantable amplification system or IAS, which includes both signal amplification components and a polymer matrix. Additionally, an important feature of the present invention is the immobilization of the amplification components in the polymer matrix. The immobilization can be carried out by physical entrapment or by covalent attachment. The second component is the optical system which utilizes transdermal or fiber optic transmission of light or signal.

Implantable Amplification Systems (IAS)

In one aspect, the present invention provides an implantable amplification system which is a combination of an analyte signal transducer or amplification components and a polymer matrix, preferably a biocompatible matrix. There are several methods for chemical amplification of an analyte signal, including enzymatic means, equilibrium-binding means and spectroscopic means.

Amplification Components

1. Enzymatic Methods

Figure 7:
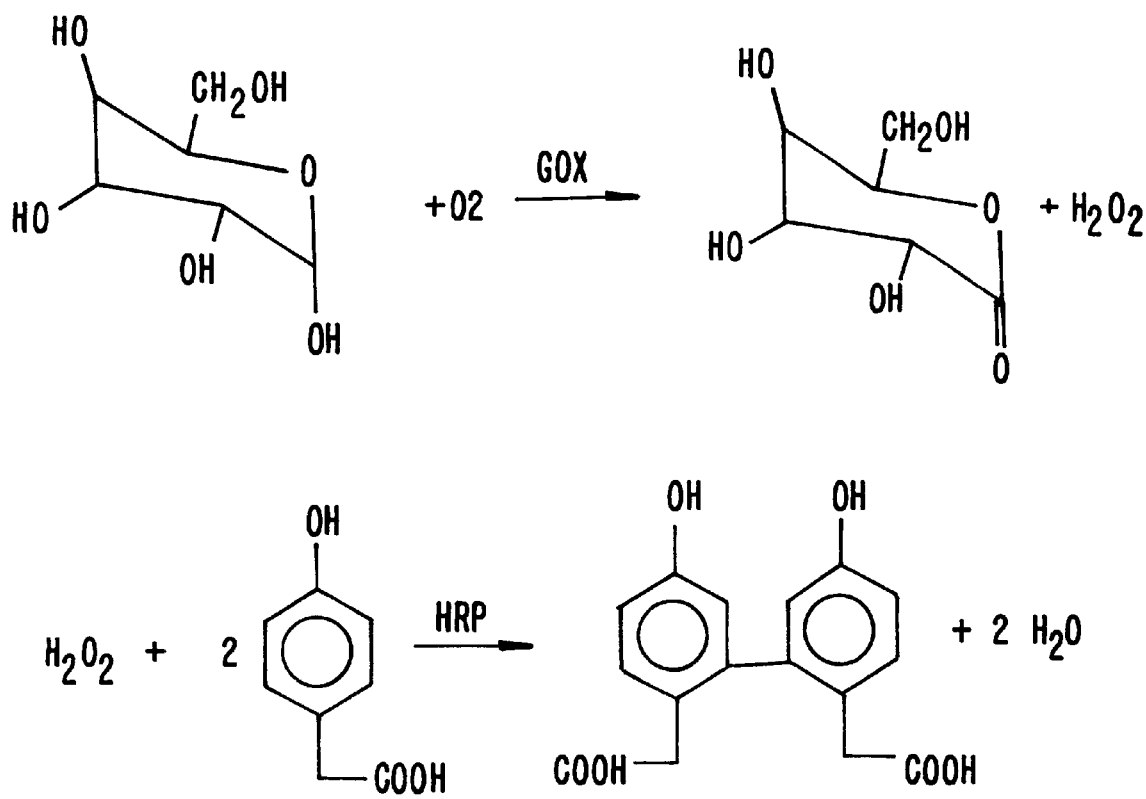
FIG. 7 shows the chemical reactions of glucose and glucose oxidase to produce hydrogen peroxide which can be detected optically.
Figure 8:
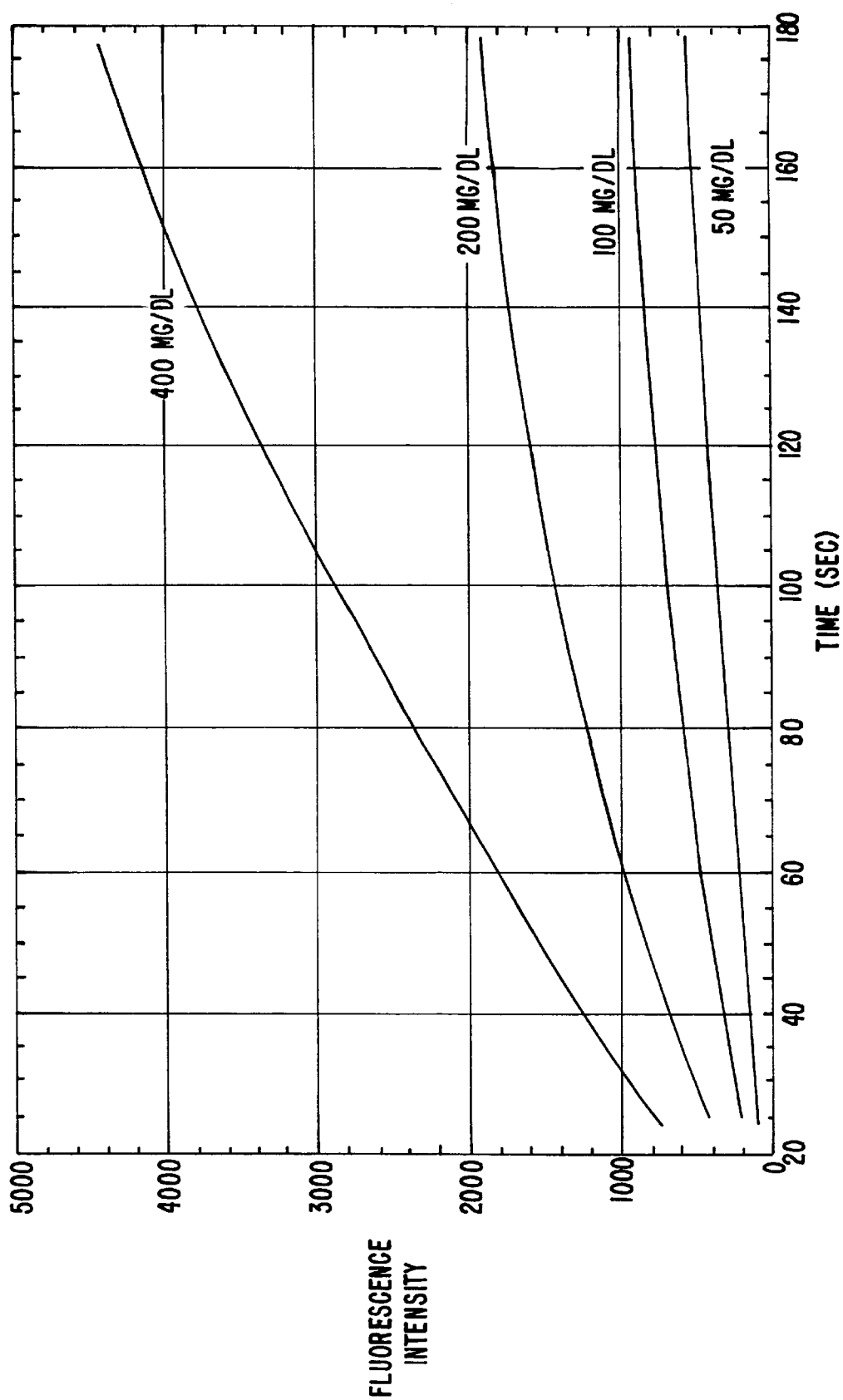
FIG. 8 shows the curves from the reaction shown in FIG. 7, namely the fluorescence intensity as a function of time for a variety of glucose concentrations.

Enzymatic methods convert glucose stoichiometrically to hydrogen peroxide, which can be affected via fluorescence, chemiluminescence or absorbance means. One such scheme uses the classical $H_2O_2$ detection scheme as described by Guilbault and coworkers. See, Guilbault, et al., *Anal. Chem.*, 40:190 (1968). In this dimerization based scheme, an optical signal due to glucose can be amplified and detected optically. The first equation in FIG. 7 shows the reaction of glucose and oxygen which is catalyzed by the enzyme glucose oxidase. The products are the lactone which immediately converts to gluconic acid, and hydrogen peroxide ($H_2O_2$). The second equation in FIG. 7 shows the reaction of the hydrogen peroxide and parahydroxyphenyl acetic acid (HPAA). This reaction is catalyzed by another enzyme, horseradish peroxidase (HRP). The product of the reaction is the dimer of the parahydroxyphenyl acetic acid. The dimer is highly fluorescent, and its fluorescence is proportional to the glucose concentration. FIG. 8 shows the curves from the reaction shown in FIG. 7. These curves show the fluorescence intensity as a function of time for a variety of glucose concentrations.

The major problem with this system however is that it is not reversible and incorporating a reducing agent into the sensor has been found to be impractical. In order to be useful as a long term transdermal sensor, the chemical amplification process must be reversible. Several candidates for reversibility are available. For example, a novel ruthenium porphyrin complex (e.g., $RuO_2$) may be included to catalyze the decomposition of the dimer after it is formed. The use of this coupled reaction scheme means that the system is truly reagentless and its lifetime in the body is limited by the physiological response to the implant.

HPAA may be modified (e.g., by diazotization) to produce a fluorescent product that is excitable at longer wavelengths. Alternatively, HPAA may be modified to form a highly fluorescent but short-lived reaction product. This would involve creating a conformationally strained intermediate such as the norbornyl cation attached to the basic HPAA backbone. Two related approaches are also possible, which can be classified as either fluorescent quenching or fluorescent enhancement approaches. In the first case, the substrate of HRP is fluorescent and the $H_2O_2$ produced by the GOX quenches this fluorescence by reacting with the substrate bound to the HRP. In the second case, the $H_2O_2$ chemically oxidizes a non-fluorescent substrate bound to the HRP that fluoresces when oxidized. $H_2O_2$ can be used to oxidize a substrate that changed color. As an example, the type of chemistry used on the reflectance strip could be immobilized on a gel and used in the transmission made in a finger web.

In addition to the fluorescence methods which can detect $H_2O_2$ (formed from the reaction shown in FIG. 7), there are two other possibilities that can be used to detect $H_2O_2$. The first is the chemiluminescence of luminol. Luminol upon oxidation by $H_2O_2$ undergoes chemiluminescence, where the intensity of the emitted light is proportional to the $H_2O_2$ concentration. The second method is to use a dye such as 3-methyl-2-benzothiazolinone hydrazone hydrochloride which turns a deep blue color in the presence of $H_2O_2$.

2. Equilibrium Binding Methods

Non-enzymatic equilibrium-based amplification methods for polyhydroxylated analyte (e.g., glucose) amplification are preferable to enzymatic ones, because the ability of an enzyme to maintain its activity over long periods of time in the body is limited. In addition, enzymatic approaches based on $O_2$ consumption (for glucose measurement) suffer from the inherent deficiency of $O_2$ vs. glucose in the body and require a differentially permeable outer membrane.

Figure 9:
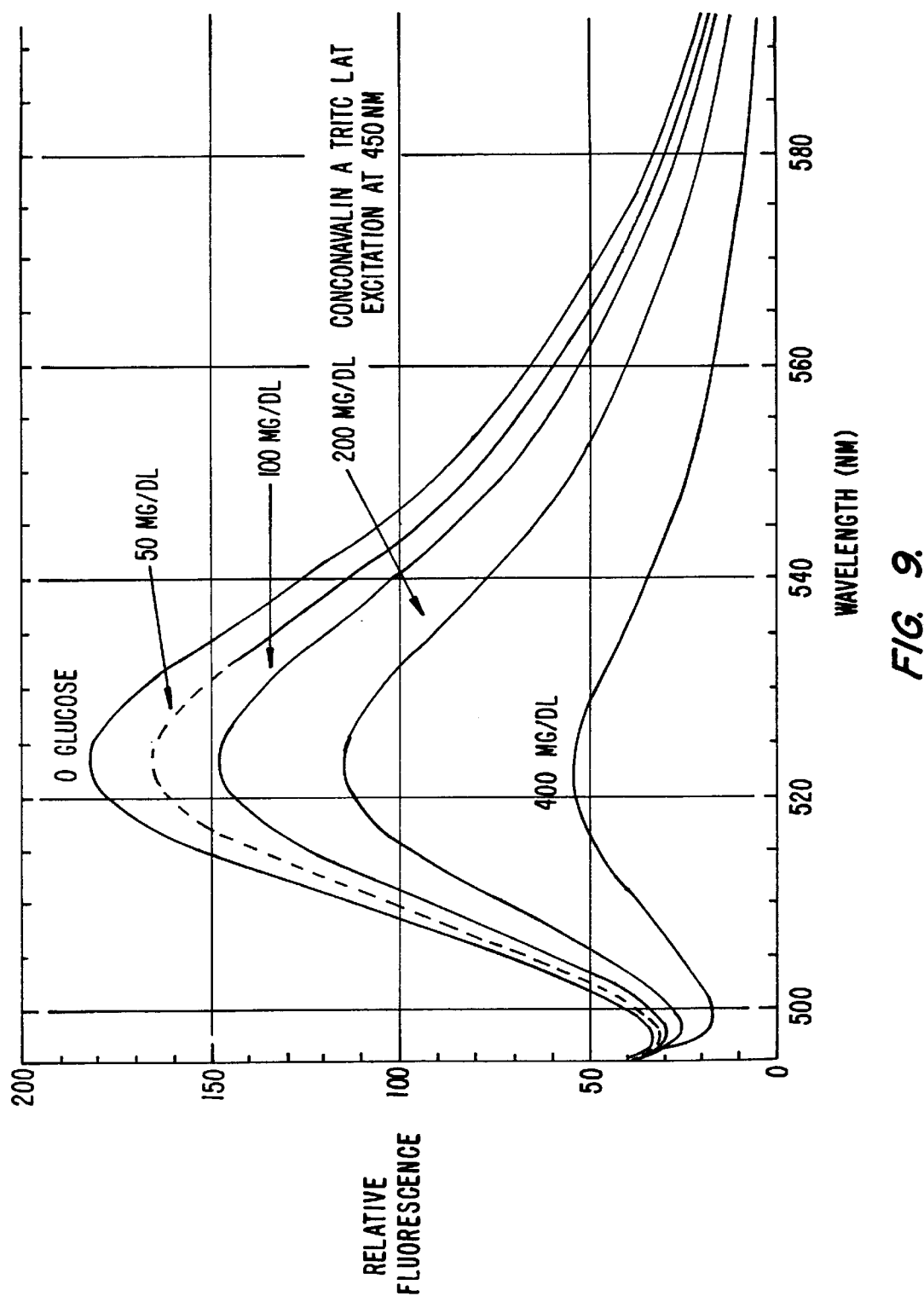
FIG. 9 shows the fluorescence spectrum of rhodamine-labeled concanavalin A in different glucose concentrations.

Non-enzymatic equilibrium based amplification methods can be based either on lectins or on boronate (germinate or arsenate) based aromatic compounds. Chick, U.S. Pat. No. 5,342,789 describes a competitive binding approach whereas the present invention uses the simpler approach of attenuation in the fluorescence intensity of labeled lectin molecules. One method utilizes a lectin such as concanavalin A (Jack Bean), *Vicia faba* (Fava Bean) or *Vicia sativa*. Such lectins bind glucose with equilibrium constants of approximately 100. See, Falasca, et al., *Biochim. Biophys. Acta.*, 577:71 (1979). Labeling of the lectin with a fluorescent moiety such as fluorescein isothiocyanate or rhodamine is relatively straightforward using commercially available kits. FIG. 9 shows the fluorescence spectrum of the rhodamine labeled concanavalin A in different glucose concentrations. The mechanism of action of the lectin fluorescence quenching is presumably due to changes in the molecular conformation of the glucose containing lectin to that without the glucose present. In the case of lectins, fluorescence quenching of a fluorescein or rhodamine label occurs via an unknown mechanism, but possibly due to the conformational change. Details for the immobilization of rhodamine labeled lectin (concanavalin A) into a polyurethane (Jeffamine/Silicone polyurethane) membrane are provided below. The fluorescence of the labeled lectin decreased with increasing glucose concentration.

Figure 10:
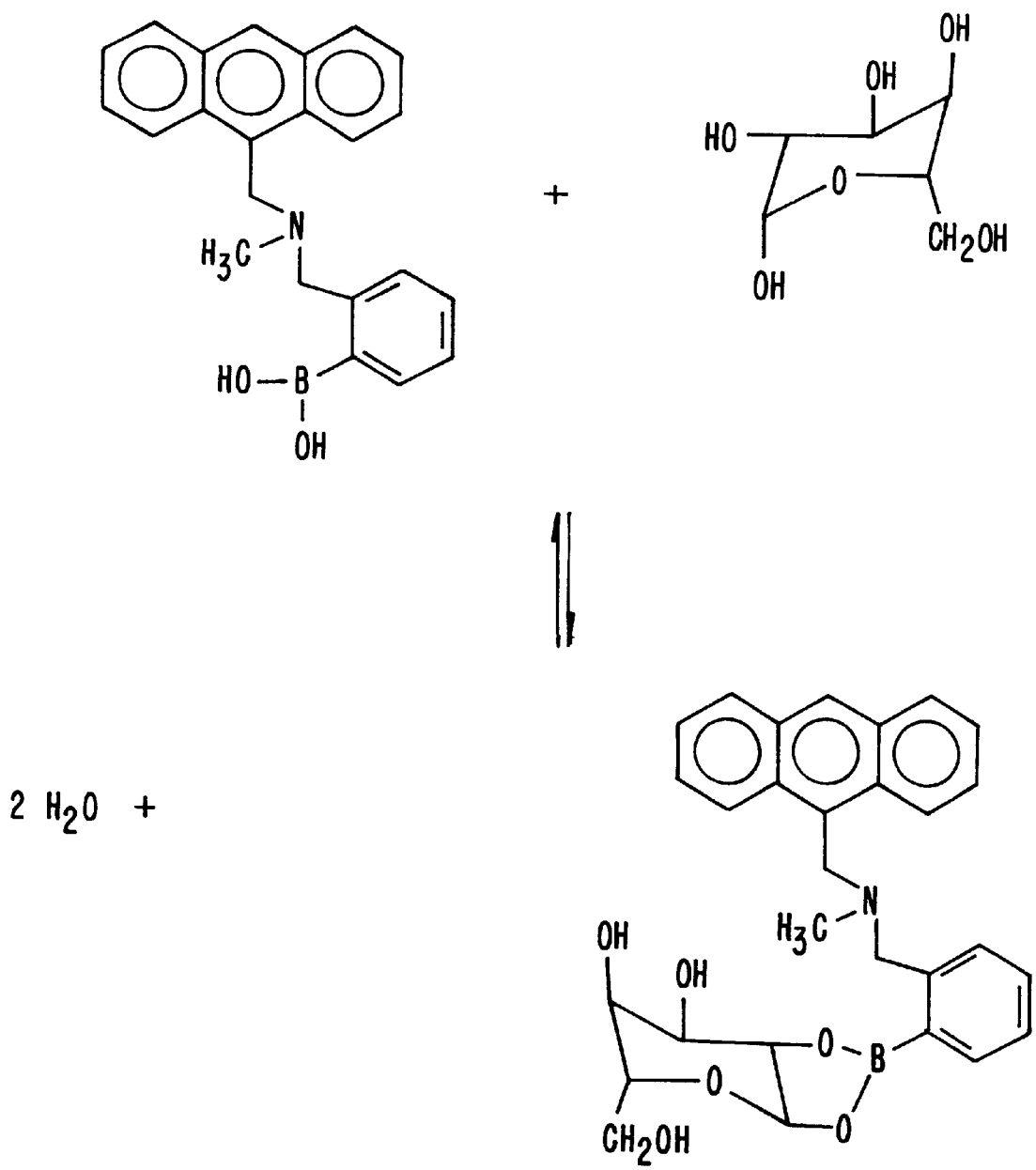
FIG. 10 shows the reversible interaction between a polyhydroxylated analyte such as glucose and a boronate complex, N-methyl-N-(9-methylene anthryl)-2-methylenephenylboronic acid.

Another equilibrium binding approach to a single substrate system that does not involve biomolecules is to use boronate based sugar binding compounds. The basic interaction between a sugar such as glucose and a labeled boronate complex is shown in FIG. 10. The binding of glucose to the boronate group is reversible as shown in FIG. 10. In one case, the fluorescence of the boronate compounds is changed upon addition of glucose. In other cases, fluorescence enhancement or quenching occurs due to intramolecular electron transfer. See, Falasca, et al., *Biochim. Biophys. Acta.*, 577:71 (1979); Nakashima and Shinkai, *Chemistry Letters*, 1267 (1994); and James, et al., *J. Chem. Soc. Chem. Commun.*, 277 (1994). In some boronate complexes, modification of the acidity of the Lewis acid boron center is changed upon glucose binding.

Boronate complexes have been described which transduce a glucose signal through a variety of means. See, Nakashima, et al., *Chem. Lett.* 1267 (1994); James, et al., *J. Chem. Soc. Chem. Commun*, 477 (1994); and James, et al., *Nature*, 374:345 (1995). These include geometrical changes in porphyrin or indole type molecules, changes in optical rotation power in porphyrins, and photoinduced electron transfer in anthracene type moieties. Similarly, the fluorescence of 1-anthrylboronic acid has been shown to be quenched by the addition of glucose. See, Yoon, et al., *J. Am. Chem. Soc.*, 114:5874 (1992). A postulated mechanism for this effect is that of a shift in the Lewis acidity of the boronate group upon complexation of a diol. All these published approaches describe signal transduction systems only.

An application to actual in vivo sensing for the above approaches must also encompass the immobilization of the transduction system into a suitable polymer system, which is preferably a biocompatible polymer. In the present invention, the transduction system, or signal amplification components are entrapped within a suitable polymer matrix. Alternatively, the amplification components can be covalently attached to, and surrounded by the polymer matrix. Covalent attachment of the components to a polymer matrix prevents leakage of the components to surrounding tissue, and other undesirable contact of the amplification components with non-target fluids.

In one group of embodiments, the amplification components comprise an arylboronic acid moiety attached to an amine-functionalized dye molecule. The linkage between the arylboronic acid moiety and the dye molecule will typically be from about two to about four carbon atoms, preferably interrupted by one or more heteroatoms such as oxygen, sulfur, phosphorus or nitrogen. Certain non-limiting examples of suitable linkages include —$CH_2$—NH—$CH_2$—, —$(CH_2)_2$—NH—$CH_2$—, —C(O)$CH_2$—NH—$CH_2$—, —$CH_2$—NR—$CH_2$—, —$(CH_2)_2$—NR—$CH_2$—, and —C(O)$CH_2$—NR—$CH_2$—, in which the R group is an alkyl substituent of from 1 to about 8 carbon atoms. As used herein the term "alkyl" refers to a saturated hydrocarbon radical which may be straight-chain or branched-chain (for example, ethyl, isopropyl, t-amyl, or 2,5-dimethylhexyl). This definition applies both when the term is used alone and when it is used as part of a compound term, such as "haloalkyl" and similar terms. Preferred alkyl groups are those containing 1 to 6 carbon atoms. All numerical ranges in this specification and claims are intended to be inclusive of their upper and lower limits. Additionally, the alkyl group which is attached to a nitrogen atom in the linkages above will preferably be substituted with a functional group such as hydroxy, amino or thiol which will facilitate the covalent attachment of the amplification component to a biocompatible matrix.

In a related group of embodiments, the implantable amplification system incorporates a compound of the formula:

(I)

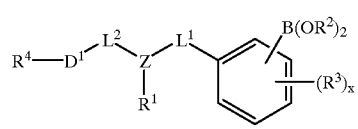

In this formula, $D^1$ represents a dye which can be a fluorescent dye, a luminescent dye or colorimetric dye. The symbols $R^1$, $R^3$ and $R^4$ each independently represent substituents which alter the electronic properties of the groups to which they are attached or which contain functional groups capable of forming covalent linkages to the surrounding polymer matrix. Preferably, $R^1$, $R^3$ and $R^4$ are each independently hydrogen, hydroxy, acyl, $C_1$–$C_4$ alkoxy, halogen, thiol, sulfonic acid, sulfonamide, sulfinic acid, nitro, cyano, carboxylic acid, a $C_1$–$C_{12}$ alkyl group, a substituted $C_1$–$C_{12}$ alkyl group, a $C_1$–$C_{12}$ alkenyl group, a substituted $C_1$–$C_{12}$ alkenyl group, a $C_1$–$C_{12}$ alkynyl group, a substituted $C_1$–$C_{12}$ alkynyl group, aryl, substituted aryl, arylalkyl, substituted arylalkyl, amine, or substituted amine. For each of the substituted species above, the substituents are preferably hydroxy, acyl, aryl, $C_1$–$C_4$ alkoxy, halogen, thiol, sulfonic acid, amines, sulfonamide, sulfinic acid, nitro, cyano, carboxamide or carboxylic acid. In particularly preferred embodiments, $R^1$, $R^3$ and $R^4$ are each independently hydrogen, hydroxy, $C_1$–$C_4$ acyl, $C_1$–$C_4$ alkoxy, halogen, thiol, sulfonic acid, sulfonamide, nitro, cyano, carboxylic acid, a $C_1$–$C_4$ alkyl group, a $C_1$–$C_4$ alkenyl group, a $C_1$–$C_4$ alkynyl group, aryl, arylalkyl, or amine.

Each of the $R^2$ symbols independently represents hydrogen or $C_1$–$C_4$ alkyl, or taken together the two $R^2$ groups form a $C_2$–$C_5$ alkylene chain. Preferably, the $R^2$ groups are both hydrogen.

Each of $L^1$ and $L^2$ independently represent a linking group having from zero to four contiguous atoms, preferably one to two. The linking groups are preferably alkylene chains (e.g., methylene, ethylene, propylene, or butylene). Alternatively, the alkylene chains can have one or more of the carbon atoms replaced by a oxygen, nitrogen, sulfur or phosphorus, with the understanding that any remaining valences on the heteroatoms can be occupied by hydrogen, hydroxy groups or oxo groups. Preferably, the heteroatoms when present, are oxygen or nitrogen.

The symbol Z represents a nitrogen, sulfur, oxygen or phosphorus. One of skill would understand that for those embodiments in which Z is oxygen, $R^1$ will not be present. Additionally, as above, any remaining valences on the heteroatoms can be occupied by hydrogen, hydroxy groups or oxo groups. Preferably, Z is nitrogen. The symbol x is an integer of from zero to four.

The chemical terms used herein are taken to have their accepted meanings to one of skill in the chemical arts. For example, the term "alkoxy" refers to an alkyl radical as described above which also bears an oxygen substituent which is capable of covalent attachment to another hydrocarbon radical (such as, for example, methoxy, ethoxy, and t-butoxy). "Halogen" is meant to include —F, —Cl, —Br and —I, although —F and —Cl are preferred. The term "alkenyl" as used herein refers to an alkyl group as described above which contains one or more sites of unsaturation. The term "alkynyl" as used herein refers to an alkyl group as described above which contains one or more carbon-carbon triple bonds. The term "aryl" refers to an aromatic substituent which may be a single ring or multiple rings which are fused together, linked covalently or linked to a common group such as an ethylene or methylene moiety. The aromatic rings may each contain heteroatoms, for example, phenyl, naphthyl, biphenyl, diphenylmethyl, 2,2-diphenyl-1-ethyl, thienyl, pyridyl and quinoxalyl. The aryl moieties may also be optionally substituted as discussed above. Additionally, the aryl radicals may be attached to other moieties at any position on the aryl radical which would otherwise be occupied by a hydrogen atom (such as, for example, 2-pyridyl, 3-pyridyl and 4-pyridyl). The term "arylalkyl" refers to an aryl radical attached directly to an alkyl group.

Figure 11:
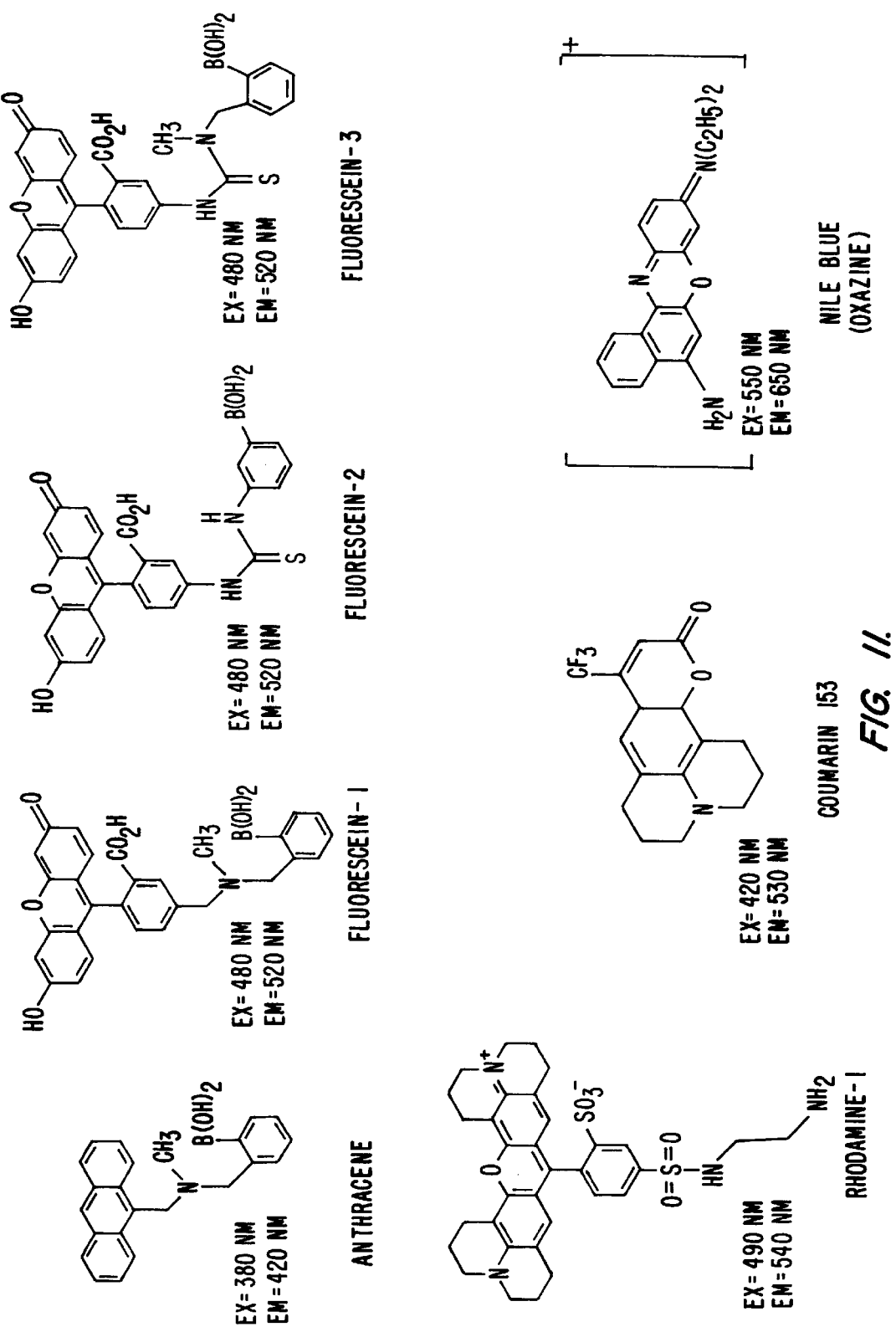
FIG. 11 provides the structures for a number of boronate compounds of formula I, along with excitation and emission wavelengths.

Preferably, the dye used in formula (I) is an anthracene, fluorescein, xanthene (e.g., sulforhodamine, rhodamine), cyanine, coumarin (e.g., coumarin 153), oxazine (e.g., Nile blue), a metal complex or other polyaromatic hydrocarbon which produces a fluorescent signal. Structures for some of the embodiments of formula I are provided in FIG. 11 along with the excitation and emission wavelengths for each. Particularly preferred are long wavelength fluorescent dyes having emission wavelengths of at least about 450 nm, preferably from 450 to about 800 nm. Shorter wavelength dyes typically do not provide sufficient signal through the skin. As a result, shorter wavelength dyes are suitable for applications in which interrogation and signal delivery is by means of a fiber optic. Preferred shorter wavelength dyes are those having emission wavelengths of about 320 nm to about 450 nm.

Figure 12:
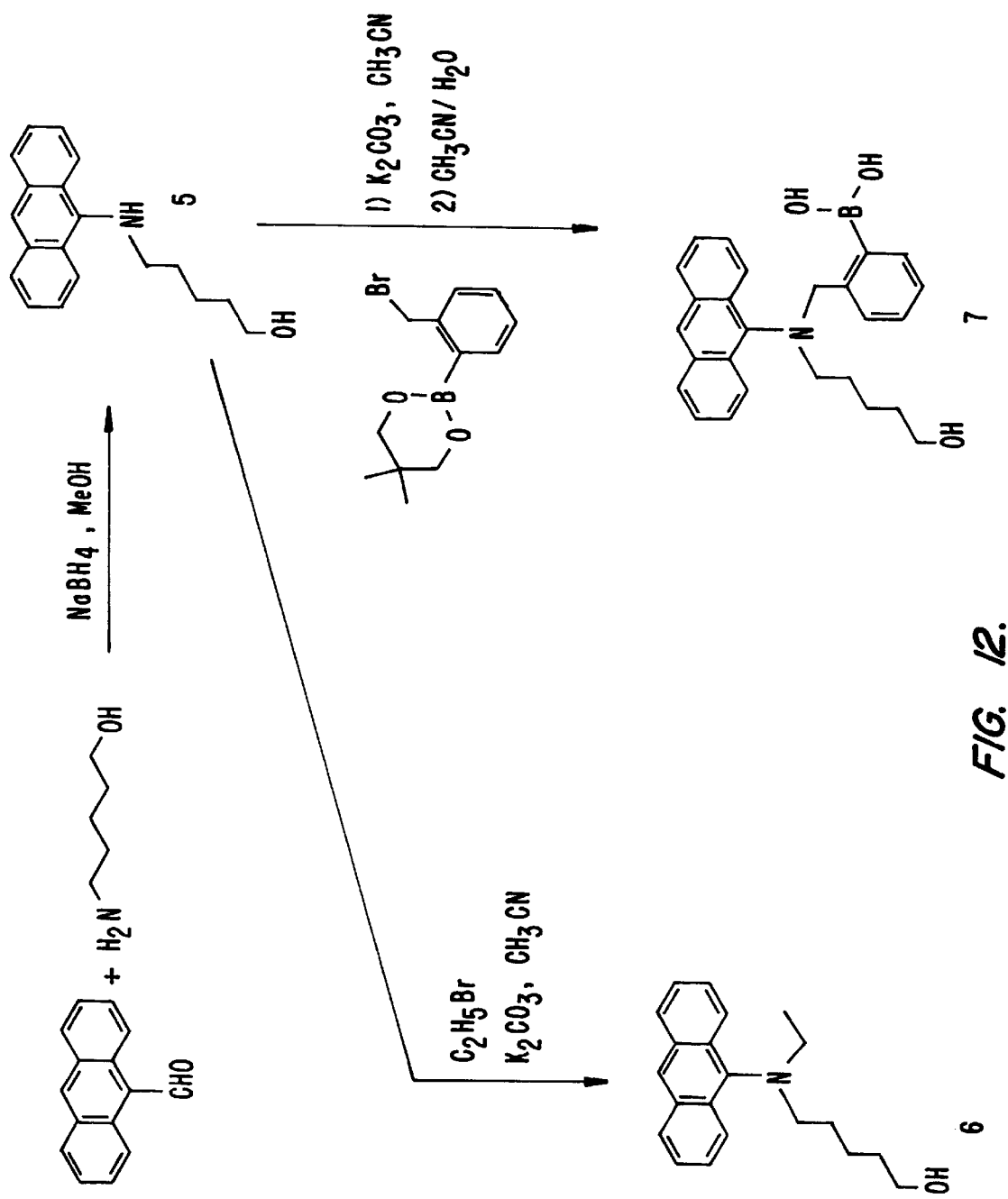
FIG. 12 illustrates a synthesis scheme for boronate complexes which are useful as amplification components.

The compounds used in this aspect of the invention can be prepared by the methods described in the examples below or by modifications thereof. FIG. 12 provides one synthesis scheme for the compounds of formula I. In this scheme, 9-anthraldehyde (available from commercial sources such as Aldrich Chemical Co., Milwaukee, Wis., USA) can be treated with 5-amino-1-pentanol (Aldrich) under reductive amination conditions using sodium borohydride in methanol. The resulting secondary amine can then be alkylated with a bromomethyl arylboronic acid derivative to provide a protected amplification component.

Figure 13:
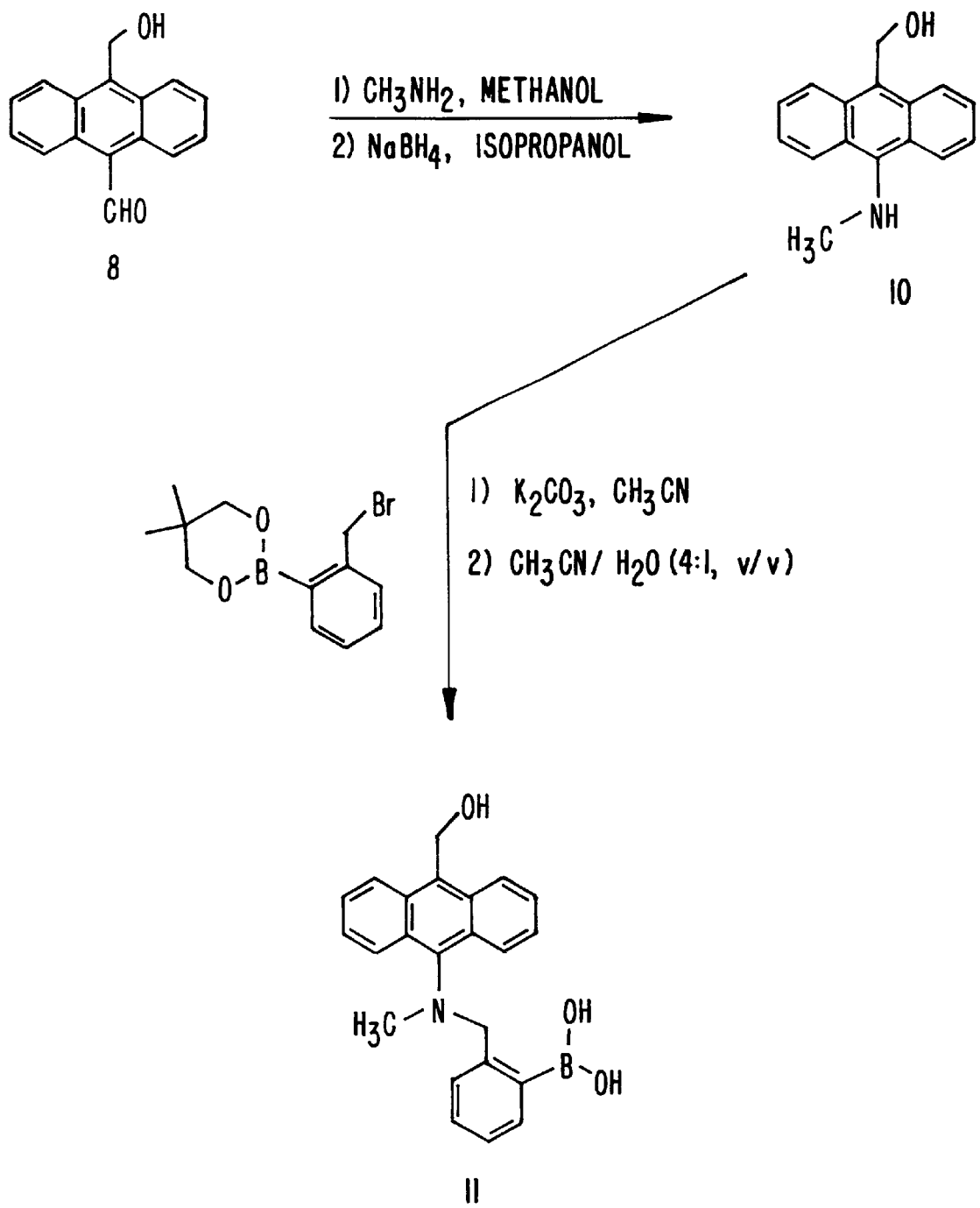
FIG. 13 illustrates another synthesis scheme for boronate complexes which are useful as amplification components.

FIG. 13 provides another synthesis scheme for the compounds of formula I. In this scheme, 10-(hydroxymethyl)-9-anthraldehyde (prepared according to the methods described in Lin, et al., *J. Org. Chem.* 44:4701 (1979)) is reductively aminated using methylamine in a two-step process involving imine formation followed by sodium borohydride reduction of the imine. Alkylation of the secondary amine with a suitable arylboronic acid derivative then provides the desired compound of formula I. In this family of compounds, the $D^1$ moiety (e.g., anthracene) has an attached hydroxymethyl group which facilitates covalent attachment of the compound to a biocompatible matrix.

3. Spectroscopic Method

Another approach to minimally invasive glucose sensing is by surface enhanced resonance Raman spectroscopy. The glucose is bound to a substrate like concanavalin A or a boric acid complex and the Raman spectrum measured.

Immobilization of the Amplification Components in a Polymer Matrix

In order to use the amplification components for analyte sensing in vivo, the components for the reactions must be immobilized in a polymer matrix that can be implanted subdermally. The matrix should be permeable to the analyte of interest and be stable within the body. Still further, the matrix should be prepared from biocompatible materials, or alternatively, coated with a biocompatible polymer. As used herein, the term "biocompatible" refers to a property of materials or matrix which produce no detectable adverse conditions upon implantation into an animal. While some inflammation may occur upon initial introduction of the implantable amplification system into a subject, the inflammation will not persist and the implant will not be rendered inoperable by encapsulation (e.g., scar tissue).

The biocompatible matrix can include either a liquid substrate (e.g., a coated dialysis tube) or a solid substrate (e.g., polyurethanes/polyureas, silicon-containing polymers, hydrogels, solgels and the like). Additionally, the matrix can include a biocompatible shell prepared from, for example, dialysis fibers, teflon cloth, resorbable polymers or islet encapsulation materials. The matrix can be in the form of a disk, cylinder, patch, microspheres or a refillable sack and, as noted, can further incorporate a biocompatible mesh that allows for full tissue ingrowth with vascularization. While subdermal implantation is preferred, one skilled in the art would realize other implementation methods could be used. The key property of the matrix is its permeability to analytes and other reactants necessary for chemical amplification of a signal. For example, a glucose monitoring matrix must be permeable to glucose. In the case of the enzymatic approach, the matrix must also be permeable to $O_2$ and be compatible with $H_2O_2$. While oxygen and glucose permeability are required to form the $H_2O_2$, hydrogen peroxide permeability is necessary for the optical sensor. Finally, the implant should be optically transparent to the light from the optical source used for interrogating the IAS.

Figure 14A:
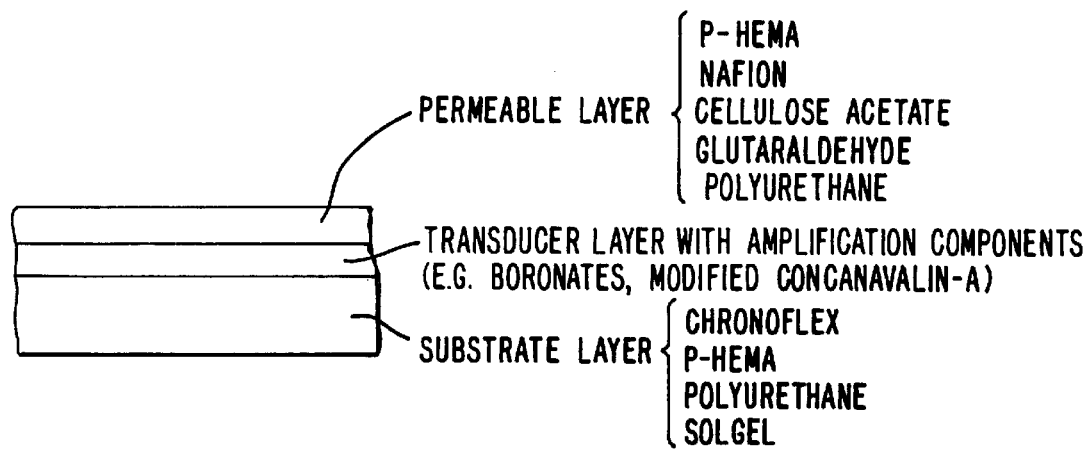
FIG. 14 provides three examples of implantable amplification systems for the immobilization of amplification components.

FIG. 14 provides an illustration of several embodiments. As seen in FIG. 14A, an amplification system can encompass a substrate layer, a transducer layer containing the amplification components, and a layer which is permeable to the analyte of interest.

The substrate layer can be prepared from a polymer such as a polyurethane, silicone, silicon-containing polymer, chronoflex, P-HEMA or sol-gel. The substrate layer can be permeable to the analyte of interest, or it can be impermeable. For those embodiments in which the substrate layer is impermeable, the amplification components will be coated on the exterior of the substrate layer and further coated with a permeable layer (see FIG. 14A).

Figure 14B:
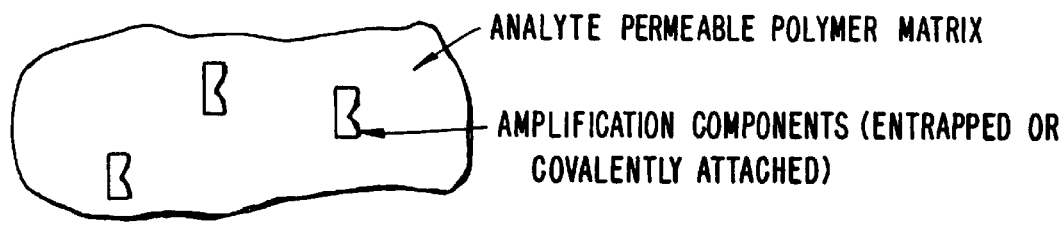
Figure 14C:
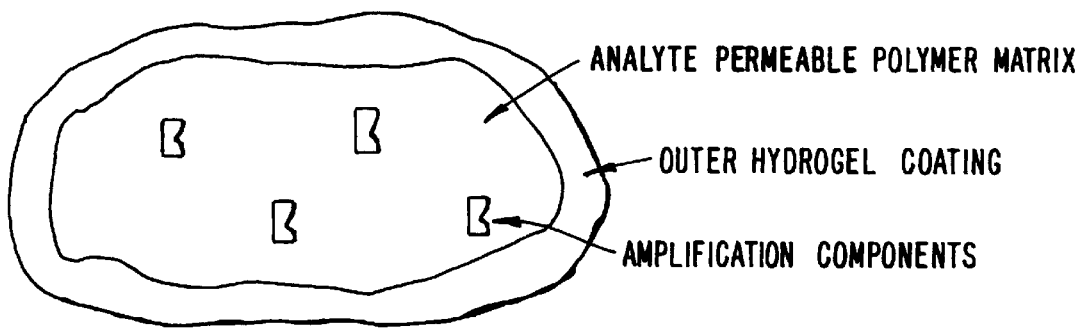

In some embodiments, the amplification components will be entrapped or encased via covalent attachment, within a matrix which is itself permeable to the analyte of interest and biocompatible (see FIG. 14B). In these embodiments, a second permeable layer is unnecessary. Nevertheless, the use of a permeable layer such as a hydrogel which further facilitates tissue implantation is preferred (see FIG. 14C).

1. Biocomnatible Matrix Materials

For those embodiments in which a polymer matrix is to be placed in contact with a tissue or fluid, the polymer matrix will preferably be a biocompatible matrix. In addition to being biocompatible, another requirement for this outermost layer of an implantable amplification system is that it be permeable to the analyte of interest. A number of biocompatible polymers are known, including some recently described silicon-containing polymers (see application Ser. No. 08/721,262, filed Sep. 26, 1996, now U.S. Pat. No. 5,777,060 and incorporated herein by reference) and hydrogels (see U.S. Pat. No. 08,749,754, filed Oct. 24, 1996, now U.S. Pat. No. 5,786, 439 and incorporated herein by reference). Silicone-containing polyurethane can be used for the immobilization of most of the glucose binding systems or other analyte amplification components. Other polymers such as silicone rubbers (NuSil 4550), biostable polyurethanes (Biomer, Tecothane, Tecoflex, Pellethane and others), PEEK (polyether ether ketone) acrylics or combinations are also suitable.

a. Silicon-Containing Polymers

In one group of embodiments, the amplification components are either entrapped in, or covalently attached to a silicone-containing polymer. This polymer is a homogeneous matrix prepared from biologically acceptable polymers whose hydrophobic/hydrophilic balance can be varied over a wide range to control the rate of polyhydroxylated analyte diffusion to the amplification components. The matrix can be prepared by conventional methods by the polymerization of diisocyanates, hydrophilic diols or diamines, silicone polymers and optionally, chain extenders. The resulting polymers are soluble in solvents such as acetone or ethanol and may be formed as a matrix from solution by dip, spray or spin coating. Preparation of biocompatible matrices for glucose monitoring have been described in application Ser No. 08/721,262, now U.S. Pat. Nos. 5,777,060, and 08/749,754, now U.S. Pat. No. 5,786, 439, the disclosures of which have previously been incorporated herein by reference.

The diisocyanates which are useful for the construction of a biocompatible matrix are those which are typically those which are used in the preparation of biocompatible polyurethanes. Such diisocyanates are described in detail in Szycher, SEMINAR ON ADVANCES IN MEDICAL GRADE POLYURETHANES, Technomic Publishing, (1995) and include both aromatic and aliphatic diisocyanates. Examples of suitable aromatic diisocyanates include toluene diisocyanate, 4,4'-diphenylmethane diisocyanate, 3,3'-dimethyl-4,4'-biphenyl diisocyanate, naphthalene diisocyanate and paraphenylene diisocyanate. Suitable aliphatic diisocyanates include, for example, 1,6-hexamethylene diisocyanate (HDI), trimethylhexamethylene diisocyanate (TMDI), trans-1,4-cyclohexane diisocyanate (CHDI), 1,4-cyclohexane bis(methylene isocyanate) (BDI), 1,3-cyclohexane bis(methylene isocyanate) ($H_6$XDI), isophorone diisocyanate (IPDI) and 4,4'-methylenebis(cyclohexyl isocyanate) ($H_{12}$MDI). In preferred embodiments, the diisocyanate is isophorone diisocyanate, 1,6-hexamethylene diisocyanate, or 4,4'-methylenebis(cycloheyl isocyanate). A number of these diisocyanates are available from commercial sources such as Aldrich Chemical Company (Milwaukee, Wis., USA) or can be readily prepared by standard synthetic methods using literature procedures.

The quantity of diisocyanate used in the reaction mixture for the present compositions is typically about 50 mol % relative to the combination of the remaining reactants. More particularly, the quantity of diisocyanate employed in the preparation of the present compositions will be sufficient to provide at least about 100% of the —NCO groups necessary to react with the hydroxyl or amino groups of the remaining reactants. For example, a polymer which is prepared using x moles of diisocyanate, will use a moles of a hydrophilic polymer (diol, diamine or combination), b moles of a silicone polymer having functionalized termini, and c moles of a chain extender, such that x=a+b+c, with the understanding that c can be zero.

A second reactant used in the preparation of the biocompatible matrix described herein is a hydrophilic polymer. The hydrophilic polymer can be a hydrophilic diol, a hydrophilic diamine or a combination thereof. The hydrophilic diol can be a poly(alkylene)glycol, a polyester-based polyol, or a polycarbonate polyol. As used herein, the term "poly(alkylene)glycol" refers to polymers of lower alkylene glycols such as poly(ethylene)glycol, poly(propylene)glycol and polytetramethylene ether glycol (PTMEG). The term "polycarbonate polyol" refers those polymers having hydroxyl functionality at the chain termini and ether and carbonate functionality within the polymer chain. The alkyl portion of the polymer will typically be composed of C2 to C4 aliphatic radicals, or in some embodiments, longer chain aliphatic radicals, cycloaliphatic radicals or aromatic radicals. The term "hydrophilic diamines" refers to any of the above hydrophilic diols in which the terminal hydroxyl groups have been replaced by reactive amine groups or in which the terminal hydroxyl groups have been derivatized to produce an extended chain having terminal amine groups. For example, a preferred hydrophilic diamine is a "diamino poly(oxyalkylene)" which is poly(alkylene)glycol in which the terminal hydroxyl groups are replaced with amino groups. The term "diamino poly(oxyalkylene" also refers to poly(alkylene)glycols which have aminoalkyl ether groups at the chain termini. One example of a suitable diamino poly(oxyalkylene) is poly(propylene glycol)bis(2-aminopropyl ether). A number of the above polymers can be obtained from Aldrich Chemical Company. Alternatively, literature methods can be employed for their synthesis.

The amount of hydrophilic polymer which is used in the present compositions will typically be about 10% to about 80% by mole relative to the diisocyanate which is used. Preferably, the amount is from about 20% to about 60% by mole relative to the diisocyanate. When lower amounts of hydrophilic polymer are used, it is preferable to include a chain extender (see below).

Silicone polymers which are useful for the determination of polyhydroxylated analytes (e.g., glucose) are typically linear. For polymers useful in glucose monitoring, excellent oxygen permeability and low glucose permeability is preferred. A particularly useful silicone polymer is a polydimethylsiloxane having two reactive functional groups (i. e, a functionality of 2). The functional groups can be, for example, hydroxyl groups, amino groups or carboxylic acid groups, but are preferably hydroxyl or amino groups. In some embodiments, combinations of silicone polymers can be used in which a first portion comprises hydroxyl groups and a second portion comprises amino groups. Preferably, the functional groups are positioned at the chain termini of the silicone polymer. A number of suitable silicone polymers are commercially available from such sources as Dow Chemical Company (Midland, Mich., USA) and General Electric Company (Silicones Division, Schenectady, N.Y., USA). Still others can be prepared by general synthetic methods known to those skilled in the art, beginning with commercially available siloxanes (United Chemical Technologies, Bristol, Pa., USA). For use in the present invention, the silicone polymers will preferably be those having a molecular weight of from about 400 to about 10,000, more preferably those having a molecular weight of from about 2000 to about 4000. The amount of silicone polymer which is incorporated into the reaction mixture will depend on the desired characteristics of the resulting polymer from which the biocompatible membrane are formed. For those compositions in which a lower analyte penetration is desired, a larger amount of silicone polymer can be employed. Alternatively, for compositions in which a higher analyte penetration is desired, smaller amounts of silicone polymer can be employed. Typically, for a glucose sensor, the amount of siloxane polymer will be from 10% to 90% by mole relative to the diisocyanate. Preferably, the amount is from about 20% to 60% by mole relative to the diisocyanate.

In one group of embodiments, the reaction mixture for the preparation of biocompatible membranes will also contain a chain extender which is an aliphatic or aromatic diol, an aliphatic or aromatic diamine, alkanolamine, or combinations thereof. Examples of suitable aliphatic chain extenders include ethylene glycol, propylene glycol, 1,4-butanediol, 1,6-hexanediol, ethanolamine, ethylene diamine, butane diamine, 1,4-cyclohexanedimethanol. Aromatic chain extenders include, for example, para-di(2-hydroxyethoxy) benzene, meta-di(2-hydroxyethoxy)benzene, Ethacure 100® (a mixture of two isomers of 2,4-diamino-3,5-diethyltoluene), Ethacure 300® (2,4-diamino-3,5-di (methylthio)toluene), 3,3'-dichloro4, 4'diaminodiphenylmethane, Polacure® 740 M (trimethylene glycol bis(para-aminobenzoate)ester), and methylenedianiline. Incorporation of one or more of the above chain extenders typically provides the resulting biocompatible membrane with additional physical strength, but does not substantially increase the glucose permeability of the polymer. Preferably, a chain extender is used when lower (i.e., 10–40 mol %) amounts of hydrophilic polymers are used. In particularly preferred compositions, the chain extender is diethylene glycol which is present in from about 40% to 60% by mole relative to the diisocyanate.

b. Hydrogels

In some embodiments, the polymer matrix containing the amplification components can be further coated with a permeable layer such as a hydrogel, cellulose acetate, P-HEMA, nafion, or glutaraldehyde. A number of hydrogels are useful in the present invention. For those embodiments in which glucose monitoring is to be conducted, the preferred hydrogels are those which have been described in U.S. Ser. No. 08/749,754, now U.S. Pat. No. 5,786,439the disclosure of which has previously been incorporated herein by reference. Alternatively, hydrogels can be used as the polymer matrix which encase or entrap the amplification components. In still other embodiments, the amplification components can be covalently attached to a hydrogel.

Suitable hydrogels can be prepared from the reaction of a diisocyanate and a hydrophilic polymer, and optionally, a chain extender. The hydrogels are extremely hydrophilic and will have a water pickup of from about 120% to about 400% by weight, more preferably from about 150% to about 400%. The diisocyanates, hydrophilic polymers and chain extenders which are used in this aspect of the invention are those which are described above. The quantity of diisocyanate used in the reaction mixture for the present compositions is typically about 50 mol % relative to the combination of the remaining reactants. More particularly, the quantity of diisocyanate employed in the preparation of the present compositions will be sufficient to provide at least about 100% of the —NCO groups necessary to react with the hydroxyl or amino groups of the remaining reactants. For example, a polymer which is prepared using x moles of diisocyanate, will use a moles of a hydrophilic polymer (diol, diamine or combination), and b moles of a chain extender, such that x=a+b, with the understanding that b can be zero. Preferably, the hydrophilic diamine is a "diamino poly(oxyalkylene)" which is poly(alkylene)glycol in which the terminal hydroxyl groups are replaced with amino groups. The term "diamino poly(oxyalkylene" also refers to poly(alkylene)glycols which have aminoalkyl ether groups at the chain termini. One example of a suitable diamino poly(oxyalkylene) is poly(propylene glycol) bis(2-aminopropyl ether). A number of diamino poly (oxyalkylenes) are available having different average molecular weights and are sold as Jeffamines® (for example, Jeffamine 230, Jeffamine 600, Jeffamine 900 and Jeffamine 2000). These polymers can be obtained from Aldrich Chemical Company. Alternatively, literature methods can be employed for their synthesis.

The amount of hydphlic polymer which is used in the present compositions will typically be about 10% to about 100% by mole relative to the diisocyanate which is used. Preferably, the amount is from about 50% to about 90% by mole relative to the diisocyanate. When amounts less than 100% of hydrophilic polymer are used, the remaining percentage (to bring the total to 100%) will be a chain extender.

Polymerization of the substrate layer components or the hydrogel components can be carried out by bulk polymerization or solution polymerization. Use of a catalyst is preferred, though not required. Suitable catalysts include dibutyltin bis(2-ethylhexanoate), dibutyltin diacetate, triethylamine and combinations thereof. Preferably dibutyltin bis(2-ethylhexanoate is used as the catalyst. Bulk polymerization is typically carried out at an initial temperature of about 25° C. (ambient temperature) to about 50° C., in order to insure adequate mixing of the reactants. Upon mixing of the reactants, an exotherm is typically observed, with the temperature rising to about 90–120° C. After the initial exotherm, the reaction flask can be heated at from 75° C. to 125° C., with 90° C. to 100° C. being a preferred temperature range. Heating is usually carried out for one to two hours.

Solution polymerization can be carried out in a similar manner. Solvents which are suitable for solution polymerization include, tetrahydrofuran, dimethylformamide, dimethyl sulfoxide, dimethylacetamide, halogenated solvents such as 1,2,3-trichloropropane, and ketones such as 4-methyl-2-pentanone. Preferably, THF is used as the solvent. When polymerization is carried out in a solvent, heating of the reaction mixture is typically carried out for at least three to four hours, and preferably at least 10–20 hours. At the end of this time period, the solution polymer is typically cooled to room temperature and poured into DI water. The precipitated polymer is collected, dried, washed with hot DI water to remove solvent and unreacted monomers, then re-dried.

2. Methods for Immobilizing the Amplification Components

Immobilization of the amplification components into a polymer matrix described above can be accomplished by incorporating the components into the polymerization mixture during formation of the matrix. If the components are prepared having suitable available functional groups the components will become covalently attached to the polymer during formation. Alternatively, the components can be entrapped within the matrix during formation.

a. Covalent Attachment

In one group of embodiments, the enzymes and substrates of the fluorescence generating reaction are immobilized in, or on the surface, of an appropriate base material using covalent bonding chemistry. The enzymes can be bonded to one component of the base polymer using any of a variety of covalent bonding techniques such as streptavidin/biotin coupling. The substrates of the fluorescence generating reaction can be covalently bonded to the base material using any of a variety of covalent bonding techniques commonly used for polymer synthesis, for example, via condensation, condensation-elimination or free radical polymerizations. For compounds of formula I, the appropriate functionalization could be accomplished at one or more of the pendant groups $R^1$, $R^3$ or $R^4$. For condensation type polymerizations, the use of a single covalent linker would lead to a terminal attachment, whereas the use of two or three R groups leads to chain extension and crosslinking, respectively. For free radical type polymerizations, chain extension can occur with a single functionalized R group.

Figure 16:
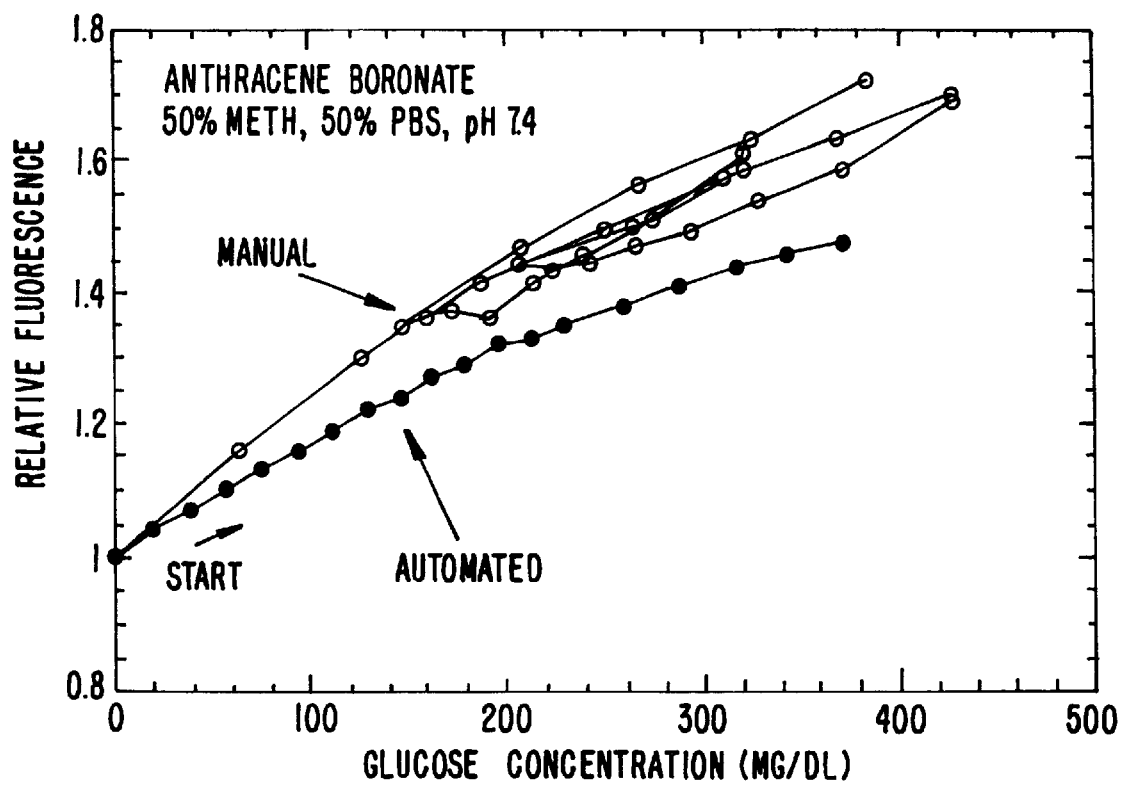
FIG. 16 shows reversible fluorescence versus glucose concentration for an anthracene boronate solation.

As outlined in Example 3, an amine-terminated block copolymer, poly(propylene glycol)-block-poly(ethylene glycol)-block-poly(propylene glycol)bis(2-aminopropyl ether), can be reacted with a diisocyanate to form a biocompatible hydrophilic polyurea. Incorporation of a hydroxy functionalized fluorescent monomer provides a polymer containing a covalently attached amplification component, in this example, as a chain terminating urethane linkage. In any case, the goal of immobilization is to incorporate the amplification components into a matrix in such a way as to retain the molecular system's desired optical and chemical activity. FIG. 16 shows the reversible change in fluorescence for a solution of anthracene-boronate as a function of glucose concentration over the physiological range.

In some embodiments, the amplification components will not be substituted with suitable functional groups for covalent attachment to a polymer during formation. In this instance, the reagents are simply entrapped. The amount of amplification component used for either the covalent or entrapped methods will typically be on the order of about 0.5% to about 10% by weight, relative to the total weight of the biocompatible matrix. One of skill in the art will understand that the amounts can be further adjusted upward or downward depending on the intensity of the signal produced as well as the sensitivity of the detector.

Optical Systems

The second aspect of the biosensors described herein consists of an optical system for interrogating the IAS and detecting the signal thus produced by the IAS. As used herein, the term "interrogating" refers to illumination of the amplification components in the IAS and subsequent detection of the emitted light. One embodiment illustrating a transdermal optical system is shown in FIG. 1, where the light source (S) shines through the skin, and a detector (D) detects the fluorescence transmitted through the skin. FIGS. 3–6 show embodiments where there is no transmission through the skin, as the light source is implanted or the light travels via a fiber optic to the amplification system positioned at the end of the fiber.

FIG. 1 shows a schematic of the subdermally implanted optical glucose monitoring system. The light source (S) could be a lamp, an LED, or a laser diode (pulsed or modulated). The detector (D) can be a photodiode, CCD detector or photomultiplier tube. Optionally, filters are used to filter the incident and/or emitted beams of light to obtain desired wavelengths. The source and detector are shown in FIG. 1 as positioned outside the body, although the source and/or the detector can be implanted as shown in FIGS. 3–6. The biocompatible material (e.g., silicone, polyurethane or other polymer) with the immobilized amplification components is implanted under the skin. The light source is used to illuminate the implanted system, and the detector detects the intensity of the emitted (typically fluorescent) light. Other modes of interaction may also be used, such as absorbance, transmittance, or reflectance, when the change in the amount of light or spectral character of the light that is measured by the detector or spectrometer is modulated by the local analyte (e.g., glucose) concentration. In yet other detection methods, the fluorescence lifetimes are measured rather than the light intensity.

In the case of fluorescence, the ratio of intensity of excitation and emission can be used to quantify the glucose signal. In a preferred embodiment, the ratio of fluorescence from the amplification components to the fluorescence of a calibration fluorophore is measured. This method eliminates errors due to registration and variations of light transport through the skin (e.g., caused by different skin tones).

Methods for the Detection and Quantitation of Analytes In Vivo

In view of the above compositions and devices, the present invention also provides methods for the detection and quantitation of an analyte in vivo. More particularly, the methods involve quantifying the amount of a polyhydroxylated analyte in an individual, by (a) interrogating a subcutaneously implanted amplification system with an energy source to provide an excited amplification system which produces an energy emission corresponding to the amount of the polyhydroxylated analyte; and (b) detecting the emission to thereby quantify the amount of the polyhydroxylated analyte in the individual.

The amplification and optical systems are essentially those which have been described above, and the preferred embodiments including components of the biocompatible matrix (e.g., silicon-containing polymers, hydrogels, etc.) are also those which have been described above. Prior to carrying out the present method, the amplification system is implanted in an individual using minimally invasive surgical or microsurgical techniques. The purpose of such implantation is to place in contact the amplification system and the analyte of interest (e.g., in fluid or tissue containing the analyte). Accordingly, the amplification system can be placed in or under the skin, or alternatively within an organ or blood vessel. When transdermal interrogation is used, the amplification system is preferably placed subcutaneously about 1–2 mm below the skin surface. For fiber optic mediated interrogation, the depth will be from 1–4 mm below the skin surface. For those embodiments in which the optical system and amplification components are in communication with an insulin pump, the placement can be at even greater depths.

The polyhydroxylated analyte can be any of a variety of endogenous or xenobiotic substances which have two or more hydroxy functional groups in positions vicinal to each other. Preferably, the analyte is a sugar, more preferably glucose.

As already noted, suitable amplification systems have been described above. However, in certain preferred embodiments, the implanted amplification system will further comprise a calibration fluorophore which provides a signal not interfering with the signal from the amplification components. In some preferred embodiments, the IAS comprises a boronate based sugar binding compound, more preferably those of formula I and a calibration fluorophore. Suitable calibration fluorophores are those fluorescent dyes such as fluoresceins, coumarins, oxazines, xanthenes, cyanines, metal complexes and polyaromatic hydrocarbons which produce a fluorescent signal. In other preferred embodiments, the amplification system will comprise a calibration fluorophore and a compound of formula I in which $D^1$ is a long wavelength fluorescent dye.

In order that those skilled in the art can more fully understand this invention, the following examples illustrating the general principles for preparation of glucose responsive systems are set forth. These examples are given solely for purposes of illustration, and should not be considered as expressing limitations unless so set forth in the appended claims. All parts are percentages by weight, unless otherwise stated.

EXAMPLES

In the examples below, Example 1 provides the synthesis of various chemical amplification components. Example 2 provides the synthesis of biocompatible polymers. Example 3 provides a description of the covalent attachment of certain amplification components to a biocompatible polymer.

General Materials and Methods

Unless otherwise noted, the materials used in the examples were obtained from Aldrich Chemical Co., Milwaukee, Wisc., USA or Sigma Chemical Company, St. Louis, Mo., USA.

Example 1

1.1 Production of para-Hydroxyphenylacetic Acid Dimer

A solution of glucose oxidase (10 U/ml) (GOX), horseradish peroxidase (1 U/ml) (HRP) and para-hydroxyphenylacetic acid were mixed in a cuvette inside a spectrofluorimeter. At time 0, an aliquot of glucose (100 mg/dl) was added and the fluorescence intensity was monitored as a function of time. FIG. 8 shows the calibration curve of glucose concentration vs. fluorescence intensity.

1.2 Synthesis of Fluorescein Labeled Boronic Acid (FABA)

Preparation of a fluorescein labeled boronic acid (FABA) was carried out as described in Uziel, et al., *Biochem. Biophys. Res. Commun.*, 180:1233 (1991), incorporated herein by reference.

Briefly, a solution (5 mL) of 3-aminophenylboronic acid was prepared in DI water. The pH was adjusted to 8 with NaOH and NaHCO$_3$. Fluorescein isothiocyanate (0.45 mmol) was added and the mixture was stirred overnight at room temperature. The fluorescein-labeled boronate was isolated as yellow crystals. At pH 10, the fluorescence of the compound was significantly decreased by the addition of glucose to the solution.

1.3 Synthesis of Labeled Boronic Acids

The labeled boronic acids described herein are prepared as outlined in the scheme depicted in FIGS. 12 and 13.

2,4,6-(o-(bromomethyl)phenyl)boroxin (1) was prepared according to a literature procedure from 2,4,6-o-Tolylboroxin substituting benzoylperoxide (BPO) for the AIBN catalyst (see, Hawkins, et al., *J. Am. Chem. Soc.* 82:3863 (1960)).

9-((N-Methyl-N-(o-boronobenzyl)amino)methyl) anthracene (2) was synthesized by a modification of a literature procedure (A)(see, James, et al., *J. Am. Chem. Soc.* 117:8982 (1995)) or by method (B).

(A): 2,4,6-(o-(bromomethyl)phenyl)boroxin (100 mg, 0.18 mmol) and 9-((methylamino)methyl)anthracene (254 mg, 1.1 mmol) were refluxed in 50 mL chloroform for 3 h. The mixture was cooled to 0° C. in an ice bath and filtered through a sintered glass frit. Solvent was removed from the filtrate under reduced pressure. The crude material was washed with 3×3 mL portions of acetonitrile/water (9/1, v/v) to remove the hydrochloride salt of 9-((methylamino) methyl)anthracene to provide 2 as a pale yellow powder: 155 mg (48%); mp 149–151° C. (lit. mp 147–152° C.); $^1$H NMR (300.13 MHz, CD$_3$OD) δ2.27 (s, 3H), 3.85 (s, 2H), 4.60 (s, 2H), 7.00–7.80 (m, 8H). 8.05 (m, 2H), 8.30–8.70 (m, 3H).

(B): A solution of 9-((methylamino)methyl)anthracene (1.00 g, 4.5 mmol), 2-bromobenzyl bromide (1.13 g, 4.5 mmol) and K$_2$CO$_3$ (0.691 g, 5.0 mmol) in 50 mL of acetonitrile was refluxed under nitrogen for 18 hr. The solution was filtered on a sintered-glass filter and solvent was removed from the filtrate under reduced pressure to yield 9-(N-Methyl-N-(o-bromobenzyl)amino)methyl) anthracene (95% by NMR). The resulting solid was taken up in diethyl ether (50 mL), and treated at 0° C. with 1 equiv of butyllithium. The mixture was stirred at 0° C. for 2 h at which time 5 equiv of trimethyborate was added via a cannula. After warming the mixture to room temperature, 50 mL of water was added to quench the reaction. The ether layer was separated, washed with 3×10 mL water, and dried over sodium sulfate. Removal of the solvent under reduced pressure provided a solid identical to that obtained in (A) in 52% yield.

2,2-Dimethylpropane-1,3-diyl(o-(bromomethyl) phenyl)boronate (3)

2,4,6-(o-(bromomethyl)phenyllboroxin (5.0 g, 25.4 mmol) and 2,2-dimethyl-1,3-propanediol (8.73 g, 83.8 mmol) were refluxed in toluene (200 mL) with azeotropic removal of water (Dean-Stark) for 24 h. The solvent was removed under vacuum to give a solid/oil mixture which was then slurried in 25 mL toluene and silica gel. The resulting mixture was filtered on a sintered-glass frit and rinsed thoroughly with cold toluene until the washings revealed no evidence of product by TLC. The combined filtrate was evaporated under reduced pressure to give 3 as a pale yellow oil: 6.76 g (94%); $^1$H NMR (300.13 MHz, CD$_3$CN) δ1.05 (s, 6H), 3.81 (s, 4H), 4.95 (s, 2H), 7.15–7.45 (m, 3H), 7.74 (m, 1H).

9,10-Bis((Methylamino)methyl)anthracene (4)

The title compound was prepared according to a literature procedure (see, James, et al., *J. Am. Chem. Soc.* 117:8982 (1995)).

9-((5-hydroxypentyl)aminomethyl)anthracene (5)

A solution of anthraldehyde (9.595 g, 0.0465 mol) and 5-amino-1-pentanol (15.00 g, 0.116 mol) dissolved in 500 mL ethanol at 0° C. was stiffed for 3 h. After warming to room temperature the solvent was removed under reduced pressure, and 150 mL of ethanol containing NaBH$_4$ (4.65 g, 0.1229 mol) was added slowly with stirring. The resulting mixture was allowed to stir overnight. The ethanol was removed under reduced pressure and to the brown oil/solid mixture was added 150 mL diethyl ether. Water was added dropwise to this solution until the evolution of hydrogen ceased, followed by the addition of 500 mL water. The ether phase was isolated, washed with 2×50 mL water, dried over sodium sulfate and filtered on a sintered-glass frit. Removal of the solvent afforded 12.17 g (89.2% yield) of 5 as a golden solid; $^1$H NMR (300.13 MHz, $CD_3CN$) δ1.51 (m, 6H), 2.81 (t, 2H), 3.49 (t, 2H), 4.68 (s, 2H), 7.52 (m, 4H), 8.05 (d, 2H), 8.44 (m, 3H); $^{13}C\text{-}\{^1H\}$ NMR (75.4 MHz, $CDCl_3$) δ133.1, 132.0, 131.7, 130.4, 128.6, 127.4, 126.2, 125.1, 62.9, 51.1, 45.8, 33.5, 30.3, 24.8.

9-((N-(5-hydroxypentyl)-N-(ethyl)amino)methyl) anthracene (6)

9-((5-hydroxypentyl)aminomethyl)anthracene (1.00 g, 3.41 mol) and $K_2CO_3$ (0.518 g, 3.75 mmol) were taken up in 25 mL acetonitrile. Ethyl bromide (11.14 g, 102 mmol) was added and the mixture was refluxed under nitrogen for 24 h. The mixture was filtered on a sintered-glass frit and the solvent and excess ethyl bromide was removed under reduced pressure. Removal of the solvent afforded 1.07 g (98% yield) of 6 as a yellow solid; $^1$H NMR (300.13 MHz, $CD_3CN$) δ1.15 (m, 2H), 1.38 (m, 5H), 1.81 (m, 2H), 3.05 (m, 4H), 3.49 (t, 2H), 5.21 (s, 2H), 7.45 (m, 2H), 7.62 (m, 2H), 8.05 (d, 2H), 8.44 (m, 3H); $^{13}C\text{-}\{^1H\}$ NMR (75.4 MHz, $CDCl_3$) δ131.8, 131.3, 130.8, 129.6, 128.0, 125.6, 124.0, 61.7, 53.1, 49.4, 48.7, 31.4, 23.9, 23.3, 10.0.

9-((N-(5-hydroxypentyl)-N-(o-boronobenzyl)amino) methyl)anthracene (7)

9-((5-hydroxypentyl)aminomethyl)anthracene (1.06 g, 3.51 mol) and $K_2CO_3$ (0.56 g, 4.05 mmol) were taken up in 15 mL acetonitrile. A solution of 2,2-dimethylpropane-1,3-diyl(o-)bromomethyl)phenyl)boronate (1.02 g, 3.51 mmol) in 5 mL acetonitrile was added and the mixture was refluxed under nitrogen for 24 h. The mixture was filtered on a sintered-glass frit and the solvent was removed under reduced pressure. The resulting solid was triturated with acetonitrile/water (4:1, v/v) to deprotect the boronate group, filtered on a sintered-glass frit and vacuum dried to yield 9 as a pale yellow solid (0.744 g, 48% yield); $^1$H NMR (300.13 MHz, $CD_3OD$) δ0.95 (m, 2H), 1.15 (m, 2H), 1.60 (m, 2H), 2.82 (m, 2H), 3.45 (m, 2H), 4.45 (s, 2H), 5.08 (s, 2H), 7.1–7.8 (m, 8H), 8.07 (d, 2H), 8.21 (d, 2H), 8.62 (s, 1H); $^{13}C\text{-}\{^1H\}$ NMR (75.4 MHz, $CDCl_3$) δ135.8, 133.0, 131.5, 129.1, 128.6, 127.8, 126.5, 124.9, 62.4, 61.9, 53.7, 49.7, 32.6, 24.9, 24.6.

10-(hydroxymethyl)-9-anthraldehyde (8) was prepared according to a literature procedure (see, Lin, et al., *J. Org. Chem.* 44:4701 (1979)).

10-(hydroxymethyl)-9-((methylimino)methyl) anthracene (9)

10-(hydroxymethyl)-9-anthraldehyde (3.00 g, 12.7 mmol) was added to 50 mL of a saturated solution of methylamine in methanol and stirred at room temperature for 2 h. The solvent and excess methylamine was removed under reduced pressure to afford the imine as a bright yellow powder (quant); $^1$H NMR (300.13 MHz, DMSO-$d_6$) δ3.35 (s, 3H), 5.51 (s, 2H), 7.61 (m, 4H), 8.55 (m, 4H), 9.48 (s, 1H).

10-(hydroxymethyl)-9-((methylamino)methyl) anthracene (10)

10-(hydroxymethyl)-9-((methylimino)methyl)anthracene (1.00 g, 4.0 mmol) was slurried in 25 mL isopropanol. $NaBH_4$ (0.454 g, 12.0 mmol) was added as a solid and the solution was stirred at room temperature for 72 h. The mixture was filtered on a sintered-glass frit and the solvent was removed under reduced pressure to yield 10 as a bright yellow powder (0.853 g, 86% yield): $^1$H NMR (300.13 MHz, $CD_3OD$) δ2.55 (s, 3H), 4.64 (s, 2H), 5.56 (s, 2H), 7.55 (m, 4H), 8.38 (m, 2H), 8.50 (m, 2H); $^{13}C\text{-}\{^1H\}$ NMR (75.4 MHz, $CD_3OD$) δ133.4, 133.0, 131.6, 131.5, 126.9, 126.7, 126.2, 125.7, 57.2, 47.9, 36.5.

10-(hydroxymethyl)-9-N-(o-boronobenzyl)amino) methylanthracene (11)

10-(hydroxymethyl)-9-((methylamino)methyl)anthracene (0.800 g, 3.18 mmol) and $K_2CO_3$ (0.56 g, 4.05 mmol) were taken up in 15 mL acetonitrile. A solution of 2,2-dimethylpropane-1,3-diyl(o-(bromomethyl)phenyl) boronate 3 (1.00 g, 3.44 mmol) in 5 mL acetonitrile was added and the mixture was refluxed under nitrogen for 24 h. The mixture was filtered hot on a sintered-glass frit and upon cooling, a yellow solid precipitated. The resulting solid was triturated with acetonitrile/water (4:1, v/v), filtered on a sintered-glass frit and vacuum dried to yield 11 as a bright yellow solid (0.632 g, 51.6% yield): $^1$H NMR (300.13 MHz, $CD_3OD$) δ2.58 (s, 3H), 4.58 (s, 2H), 5.22 (s, 2H), 5.61 (s, 2H), 7.62 (m, 6H), 7.80 (m, 2H), 8.18 (m, 2H), 8.58 (m, 2H); $^{13}C\text{-}\{^1h\}$ NMR (75.4 MHz, $CD_3OD$) δ136.9, 136.2, 135.9, 132.9, 132.7, 131.4, 129.9, 128.3, 127.1, 126.8, 126.5, 124.9, 124.1, 63.8, 57.1, 50.9, 40.7.

Example 2

This example provides the preparation of polymers used for the immobilization of the amplification components.

2.1 Biocompatible Polymers (Silicone-Containing polymers and Hydrogel Coatings)

2.1a Silicone-Containing Polymers

Synthesis of a Biocompatible Silicone/Polyurethane Patch Material for Subdermal Implantation To an oven-dried, 100 mL, 3-neck round bottom flask fitted with a mechanical stirrer, condenser, and under nitrogen was added 65 mL of anhydrous THF, 80 mg of dibutyltin dilaurate (catalytic), 5.05 grams of poly(propylene glycol-b-ethylene glycol-b-propylene glycol) bis(2-aminopropyl ether) (8.4 mmol, 0.75 equiv.), 7.01 grams polydimethylsiloxane, aminopropyldimethyl-terminated (average MW 2500) (2.8 mmol, 0.25 equiv.), and 2.94 grams of 4,4'-methylenebis(cyclohexylisocyanate) (11.2 mmol, 1 equiv.) dried over 4Å molecular sieves. An initial exotherm raised the temperature from 26 to 39° C. The reaction solution was heated at reflux for about 15 hours, the heat was removed, and the solution was allowed to cool to room temperature. The cooled solution, now visibly more viscous, was poured into approximately 900 mL of rapidly stirring DI water. The precipitated polymer was collected and washed again in approximately 800 mL DI water. The collected polymer was dried in vacuo at 80° C.

Other suitable silicone-containing polymers are described in co-pending application Ser. No. 08/721,262, now U.S. Pat. No. 5,777,060.

A bulk polymerization method of polymer formation was carried out with isophorone diisocyanate, PEG 600, diethylene glycol and aminopropyl terminated polydimethyl siloxane as follows.

Isophorone diisocyanate (4.44 g, 20 mmol, 100 mol %) was dried over molecular sieves and transferred to a 100 mL round bottom flask fitted with a nitrogen purge line and a reflux condenser. PEG 600 (2.40 g, 4.0 mmol, 20 mol %), diethylene glycol (1.06 g, 10 mmol, 50 mol %) and aminopropyl terminated polydimethylsiloxane (15 g, 6.0 mmol, 30 mol %, based on a 2500 average molecular weight) were added to the flask. Heating was initiated using a heating mantle until a temperature of 50° C. was obtained. Dibutyltin bis(2-ethylhexanoate) (15 mg) was added and the temperature increased to about 95° C. The solution was continuously stirred at a temperature of 65° C. for a period of 4 hr during which time the mixture became increasingly viscous. The resulting polymer was dissolved in 50 mL of hot THF and cooled. After cooling, the solution was poured into 5 L of stirring DI water. The precipitated polymer was torn into small pieces and dried at 50° C. until a constant weight was achieved.

A solution polymerization method using 1,6-hexamethylene diisocyanate, PEG 200 and aminopropyl terminated polydimethylsiloxane was carried out as follows.

Dried 1,6-hexamethylene diisocyanate (1.34 g, 8 mmol, 100 mol %) was added to a 100 mL 3-neck flask containing 20 mL of dry THF. PEG 200 (0.8 g, 4.0 mmol, 50 mol %) was added with stirring followed by addition of aminopropyl terminated polydimethylsiloxane (10 g, 4.0 mmol, 50 mol %). The resulting solution was warmed to 50° C. and dibutyltin bis(2-ethylhexanoate) (about 15 mg) was added. After an initial temperature rise to 83° C., the mixture was warmed and held at 70° C. for 12 hr, during which time the mixture had become very viscous. After cooling, the mixture was poured into 3 L of rapidly stirring DI water. The precipitated polymer was collected, washed with DI water (3×), torn into small pieces and dried at 50° C. until a constant weight was obtained.

Table 1 provides five formulations for representative polymers are suitable in biocompatible matrices. The polymers were prepared by solution polymerization.

TABLE 1

Representative Polymer Formulations

| Polymer | Diisocyanate | Poly(alkylene glycol) | Aliphatic diol | Siloxane |
|---|---|---|---|---|
| 1 | 1,6-Hexamethylene | PEG 600 (20%) | DEG (60%) | Aminopropyl (20%) |
| 2 | Isophorone | PEG 600 (20%) | DEG (50%) | Aminopropyl (30%) |
| 3 | 1,6-Hexamethylene | PEG 600 (50%) | None | Aminopropyl (50%) |
| 4 | 1,6-Hexamethylene | PEG 400 (40%) | None | Aminopropyl (60%) |
| 5 | 1,6-Hexamethylene | PEG 600 (60%) | None | Aminopropyl (40%) |

2.1b Hydrogel Coatings and Polymers

Hydrogels suitable for use as biosensor coatings were prepared by combining a diisocyanate with an equivalent molar amount of a hydrophilic diol or diamine or with a combination of diol or diamine and chain extender such that the molar amount of the combination was equivalent to the diisocyanate. The polymerizations were carried out in a one-pot reaction using THF as solvent and a trace catalyst (tributyltin ethylhexanoate). The reactions were heated to reflux and held at this temperature overnight (about 16 hours). The resulting polymer solution was poured into a large volume of DI water at about 20° C. and then filtered, dried, and washed with boiling DI water. The resulting polymer was again dried then taken up in 2-propanol (as a 5 wt % solution) and used for encasing an amplification component.

Formulations of representative hydrogel coatings and polymers are provided in Table 2.

TABLE 2

Representative Polymer Formulations

| Polymer | Diisocyanate | Hydrophilic diol or diamine | Chain Extender |
|---|---|---|---|
| 1 | 1,6-Hexamethylene | Jeffamine 600 (95%) | Butanediol (5%) |
| 2 | 1,6-Hexamethylene | Jeffamine 2000 (100%) | None |
| 3 | 1,6-Hexamethylene | Jeffamine 2000 (90%) | Butanediol (10%) |
| 4 | 1,6-Hexamethylene | PEG 2000 (90%) | Butanediol (10%) |
| 5 | 1,6-Hexamethylene | Jeffamine 230 (30%) | Ethylene diamine (70%) |
| 6 | 1,6-Hexamethylene | PEG 600 (75%) | Ethylene diamine (25%) |
| 7 | Isophorone | PEG 600 (75%) | Butanediol (25%) |
| 8 | Isophorone | Jeffamine 900 (70%) | 1,6-Diaminohexane (25%) |
| 9 | Isophorone | Jeffamine 900 (50%) | 1,2-Diaminocyclohexane (50%) |
| 10 | Isophorone | Jeffamine 900 (50%) | Isophorone diamine (50%) |

2.2 Incorporation of Amplification Components into a Biocompatible Matrix 2.2a Incorporation of FABA (fluorescein labeled boronic acid) into a Membrane.

Figure 15:
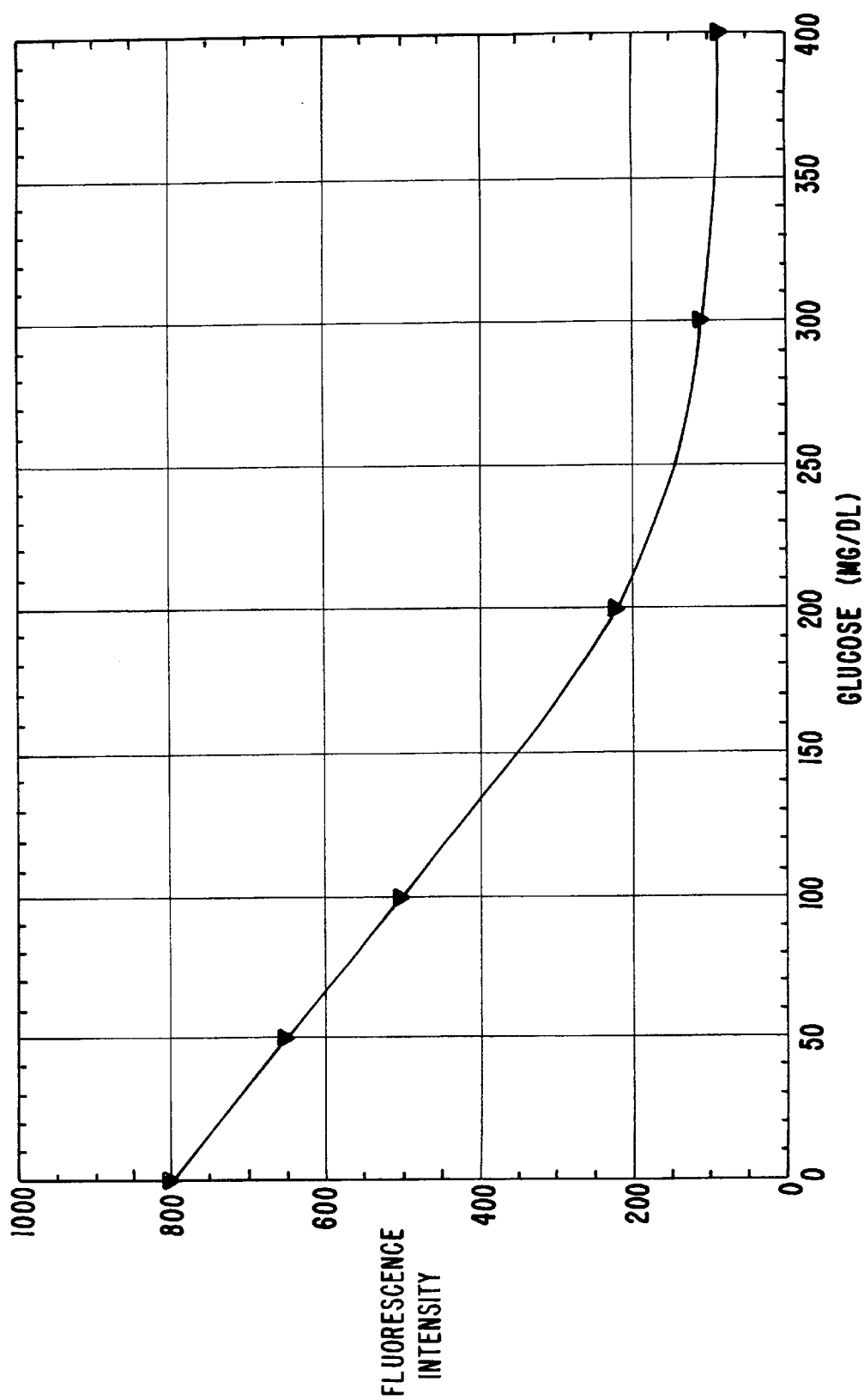
FIG. 15 provides a calibration curve for the quenching of fluorescence intensity by glucose at pH 7.4.

The fluorescence of FABA is pH sensitive. In order to measure the fluorescence quenching due to the addition of glucose, a method was developed to incorporate the FABA in a polymeric membrane at pH 10. A 7% by weight solution of a hydrophilic polyurethane was made in 2-propanol. This base solution was combined with a 0.2 mmol solution of FABA dissolved in pH 10.0 phosphate buffer 0.1M). The final concentration of the membrane was approximately 5% by weight. A membrane was cast by spreading 3 ml of the solution onto a glass plate and allowing the membrane to dry. A portion of the membrane was then attached to a thin piece of glass and placed in the diagonal of a fluorescence cuvette. Fluorescence spectra were run in pH 7.4 buffer solution. FIG. 15 shows the calibration curve generated from this experiment. As seen, the fluorescence intensity is quenched by the glucose at pH 7.4.

Example 3

This example provides the description of covalent attachment of certain components to biocompatible polymers.

Incorporation of (6) Into a Hydrophilic Polymer via a Urethane Linkage

To a three-necked 200 mL flask equipped with a condenser and a teflon stir bar was added 60 mL of dry THF, poly(propylene glycol)-block-poly(ethylene glycol)-block-poly(propylene glycol)bis(2-aminopropyl ether) (ave. Mn ca. 900, Jeffamine 900®) (6.30 g, 7.0 mmol), and dibutyltin bis(2-ethylhexanoate) catalyst (0.052 g). While stirring, 2.49 g (9.5 mmol) of 4,4'-methylenebis(cyclohexylisocyanate) was added and the resulting mixture was allowed to stir at room temperature overnight. 9-((5-hydroxy-pentyl) aminomethyl)anthracene (0.32 g, 1.0 mmol) was added and the mixture was refluxed for 2 h. The flask was removed from the heat, and the stir bar was replaced with a mechanical stirrer. 1,6-hexamethylenediamine (0.29 g, 2.5 mmol) in 2 mL THF was added to the solution with stirring and then refluxed for 1.5 h. The viscous mass was added to 500 mL water to produce an amber colored solid which was air dried on a Buchner funnel and placed in a vacuum oven overnight. Films of the polymer were prepared by casting ethanol solutions (1 g polymer/10 mL ethanol) on glass plates and air drying.

Incorporation of (7) Into a Hydrophilic Polymer via a Urethane Linkage

To a three-necked 200 mL flask equipped with a condenser and a teflon stir bar was added 60 mL of dry THF, poly(propylene glycol)-block-poly(ethylene glycol)-block-poly(propylene glycol)bis(2-aminopropyl ether) (ave. Mn ca. 900, Jeffamine 900®) (6.30 g, 7.0 mmol), and dibutyltin bis(2-ethylhexanoate) catalyst (0.052 g). While stirring, 2.49 g (9.5 mmol) of 4,4'-methylenebis(cyclohexylisocyanate) was added and the resulting mixture was allowed to stir at room temperature overnight. 9-((5-hydroxy-pentyl)-N-(o-boronobenzyl)amino)methyl)anthracene (0.44 g, 1.0 mmol) was added and the mixture was refluxed for 2 h. The flask was removed from the heat, and the stir bar was replaced with a mechanical stirrer. 1,6-hexamethylenediamine (0.29 g, 2.5 mmol) in 2 mL THF was added to the solution with stirring and then refluxed for 1.5 h. The viscous mass was added to 500 mL water to produce an amber colored solid which was air dried on a Buchner funnel and placed in a vacuum oven overnight. Films of the polymer were prepared by casting ethanol solutions (1 g polymer/10 mL ethanol) on glass plates and air drying.

Incorporation of (11) Into a Hydrophilic Polymer via a Urethane Linkage

To a three-necked 200 mL flask equipped with a condenser and a teflon stir bar was added 60 mL of dry THF, poly(propylene glycol)-block-poly(ethylene glycol)-block-poly(propylene glycol)bis(2-aminopropyl ether) (ave. Mn ca. 900, Jeffamine 900®) (0.63 g, 0.7 mmol), and dibutyltin bis(2-ethylhexanoate) catalyst (0.0052 g). While stirring, 0.249 g (0.95 mmol) of 4,4'-methylenebis (cyclohexylisocyanate) was added and the resulting mixture was allowed to stir at room temperature overnight. 10-(hydroxymethyl)-9-N-(o-boronobenzyl)amino)methyl) anthracene (0.04 g, 0.1 mmol) was added and the mixture was refluxed for 2 h. The flask was removed from the heat, and the stir bar was replaced with a mechanical stirrer. 1,6-hexamethylenediamine (0.029 g, 0.25 mmol) in 2 mL THF was added to the solution with stirring and then refluxed for 1.5 h. The viscous mass was added to 500 mL water to produce an amber colored solid which was air dried on a Buchner funnel and placed in a vacuum oven overnight. Films of the polymer were prepared by casting ethanol solutions (1 g polymer/10 mL ethanol) on glass plates and air drying.

The above description is illustrative and not restrictive. Many variations of the invention will become apparent to those of skill in the art upon review of this disclosure. Merely by way of example a variety of solvents, membrane formation methods, and other materials may be used without departing from the scope of the invention. The scope of the invention should, therefore, be determined not with reference to the above description, but instead should be determined with reference to the appended claims along with their full scope of equivalents.

All publications, patents and patent applications mentioned in this specification are herein incorporated by reference into the specification to the same extent as if each individual publication, patent or patent application was specifically and individually indicated to be incorporated herein by reference.

What is claimed is:

1. A method of immobilizing a boronic acid moiety in a solid support, the method comprising:
   covalently attaching the boronic acid moiety to a solid support comprising a polymer matrix, wherein the boronic acid moiety comprises a compound of the formula:

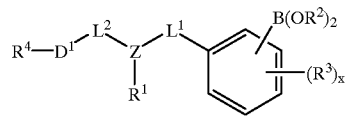

wherein $D^1$ is a dye selected from the group consisting of fluorescent dyes, luminescent dyes and colorimetric dyes;

$R^1$, $R^3$ and $R^4$ are each independently substituents which can alter the electronic properties of the groups to which they are attached or are functional groups which can form covalent linkages to the polymer matrix;

each $R^2$ is a member independently selected from the group consisting of hydrogen and $C_1$–$C_4$ alkyl;

each $L^1$ and $L^2$ is a linking group having from zero to four contiguous atoms selected from the group consisting of carbon, oxygen, nitrogen, sulfur and phosphorus;

Z is a heteroatom selected from the group consisting of nitrogen, sulfur, oxygen and phosphorus;

x is an integer from zero to four; and wherein the boronic acid moiety is attached to the polymer matrix by a covalent linkage to $R^1$.

2. The method according to claim 1, wherein said solid support is a biocompatible membrane.

3. The method according to claim 1, wherein said solid support is implantable within the body.

4. The method of claim 1, wherein the boronic acid moiety is attached to the polymer matrix using a covalent bonding technique selected from the group consisting of condensation, condensation-elimination and free radical polymerization.

5. A method of immobilizing a boronic acid moiety in a solid support, the method comprising:
   covalently attaching the boronic acid moiety to a solid support comprising a polymer matrix, wherein the boronic acid moiety comprises a compound of the formula:

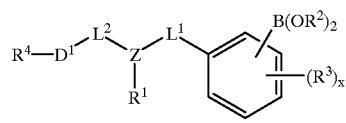

wherein $D^1$ is a dye selected from the group consisting of fluorescent dyes, luminescent dyes and colorimetric dyes;

$R^1$, $R^3$ and $R^4$ are each independently substituents which can alter the electronic properties of the groups to which they are attached or are functional groups which can form covalent linkages to the polymer matrix;

each $R^2$ is a member independently selected from the group consisting of hydrogen and $C_1$–$C_4$ alkyl;

each $L^1$ and $L^2$ is a linking group having from zero to four contiguous atoms selected from the group consisting of carbon, oxygen, nitrogen, sulfur and phosphorus;

Z is a heteroatom selected from the group consisting of nitrogen, sulfur, oxygen and phosphorus;

x is an integer from zero to four; and wherein the boronic acid moiety is attached to the polymer matrix by a covalent linkage to $R^3$.

6. The method of claim 5, wherein the boronic acid moiety is attached to the polymer matrix using a covalent bonding technique selected from the group consisting of condensation, condensation-elimination and free radical polymerization.

7. The method according to claim 5, wherein said solid support is a biocompatible membrane.

8. The method according to claim 5, wherein said solid support is implantable within the body.

9. A method of immobilizing a boronic acid moiety in a solid support, the method comprising:

covalently attaching the boronic acid moiety to a solid support comprising a polymer matrix, wherein the boronic acid moiety comprises a compound of the formula:

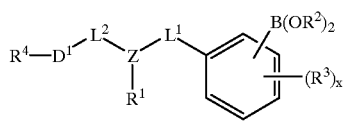

wherein $D^1$ is a dye selected from the group consisting of fluorescent dyes, luminescent dyes and colorimetric dyes;

$R^1$, $R^3$ and $R^4$ are each independently substituents which can alter the electronic properties of the groups to which they are attached or are functional groups which can form covalent linkages to the polymer matrix;

each $R^2$ is a member independently selected from the group consisting of hydrogen and $C_1$–$C_4$ alkyl;

each $L^1$ and $L^2$ is a linking group having from zero to four contiguous atoms selected from the group consisting of carbon, oxygen, nitrogen, sulfur and phosphorus;

Z is a heteroatom selected from the group consisting of nitrogen, sulfur, oxygen and phosphorus;

x is an integer from zero to four; and wherein the boronic acid moiety is attached to the polymer matrix by a covalent linkage to $R^4$.

10. The method of claim 9, wherein the boronic acid moiety is attached to the polymer matrix using a covalent bonding technique selected from the group consisting of condensation, condensation-elimination and free radical polymerization.

11. The method according to claim 9, wherein said solid support is a biocompatible membrane.

12. The method according to claim 9, wherein said solid support is implantable within the body.

13. A method of immobilizing a boronic acid moiety in a solid support, the method comprising:

entrapping the boronic acid moiety in a solid support comprising a polymer matrix, wherein the boronic acid moiety comprises a compound of the formula:

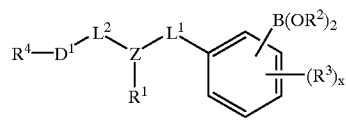

wherein $D^1$ is a dye selected from the group consisting of fluorescent dyes, luminescent dyes and colorimetric dyes;

$R^1$, $R^3$ and $R^4$ are each independently substituents which can alter the electronic properties of the groups to which they are attached or are functional groups which can form covalent linkages to the polymer matrix;

each $R^2$ is a member independently selected from the group consisting of hydrogen and $C_1$–$C_4$ alkyl;

each $L^1$ and $L^2$ is a linking group having from zero to four contiguous atoms selected from the group consisting of carbon, oxygen, nitrogen, sulfur and phosphorus;

Z is a heteroatom selected from the group consisting of nitrogen, sulfur, oxygen and phosphorus; and x is an integer from zero to four.

* * * * *